US012751935B2

(12) United States Patent
D'Souza

(10) Patent No.: US 12,751,935 B2
(45) Date of Patent: Oct. 6, 2026

(54) METHOD OF TREATING AND AMELIORATING DEPRESSION

(71) Applicants: YALE UNIVERSITY, New Haven, CT (US); The United States Government as represented by the Department of Veterans Affairs, Washington, DC (US)

(72) Inventor: Deepak Cyril D'Souza, New Haven, CT (US)

(73) Assignees: Yale University, New Haven, CT (US); The United States Government as represented by the Department of Veterans Affairs, Washington, DC (US)

( * ) Notice: Subject to any disclaimer, the term of this patent is extended or adjusted under 35 U.S.C. 154(b) by 572 days.

(21) Appl. No.: 18/308,357

(22) Filed: Apr. 27, 2023

(65) Prior Publication Data

US 2023/0346718 A1 Nov. 2, 2023

Related U.S. Application Data

(60) Provisional application No. 63/335,400, filed on Apr. 27, 2022.

(51) Int. Cl.

| | |
|---|---|
| ***A61K 31/137*** | (2006.01) |
| ***A61B 5/16*** | (2006.01) |
| ***A61P 25/24*** | (2006.01) |
| ***G16H 20/10*** | (2018.01) |

(52) U.S. Cl.

CPC ............ *A61K 31/137* (2013.01); *A61B 5/165* (2013.01); *A61P 25/24* (2018.01); *G16H 20/10* (2018.01)

(58) Field of Classification Search

CPC ....... A61K 31/137; G16H 20/10; A61P 25/24; A61B 5/165

See application file for complete search history.

(56) References Cited

U.S. PATENT DOCUMENTS

| | | | | |
|---|---|---|---|---|
| 11,406,619 | B2 † | 8/2022 | Layzell | |
| 2021/0395201 | A1 * | 12/2021 | Rands | C07D 209/16 |
| 2022/0062238 | A1 * | 3/2022 | Layzell | A61K 31/4045 |
| 2023/0346718 | A1 | 11/2023 | D'Souza | |

FOREIGN PATENT DOCUMENTS

| | | | |
|---|---|---|---|
| CA | 3127854 | † | 8/2020 |
| WO | 2022031566 | A1 | 2/2022 |
| WO | 2022043227 | A1 | 3/2022 |
| WO | 2022082058 | A1 | 4/2022 |
| WO | 2022212854 | | 10/2022 |
| WO | 2023283386 | | 1/2023 |

OTHER PUBLICATIONS

Small Pharma Ltd (2020), SPL026 (DMT Fumarate) in Healthy Subjects and MDD patients, (Publ'd Dec. 17, 2020) (Year: 2020).*

Leucht et al., Translating the HAM-D into the MADRS and Vice Versa with Equipercentile Linking, 226 J. of Affective Disorders 326-331 (2018) (Year: 2018).*

Osório, et al. "Antidepressant effects of a single dose of ayahuasca in patients with recurrent depression: a preliminary report." Brazilian Journal of Psychiatry 37 (2015): 13-20.

Palhano-Fontes, et al. "Rapid antidepressant effects of the psychedelic ayahuasca in treatment-resistant depression: a randomized placebo-controlled trial." Psychological medicine 49.4 (2019): 655-663.

International Search Report and Written Opinion issued in International Application No. PCT/US2024/020704, mailing date of Jul. 3, 2024 (pp. 1-15).

Arcee, "Mainlining into Peaceful Transcendence", Apr. 27, 2020, Erowid, httpslterowid, org/experiencestexp.php?ID=101186.

Barker, Steven A., "N, N-Dimethyltryptamine (DMT), an Endogenous Hallucinogen: Past, Present, and Future Research to Determine Its Roie and Function", vol. 12, pp. 1-17, Aug. 2018, Frontiers in Ne,uroscience.

BioSpace, "Small Pharrna Inc,: World's First Clinical Trial for DMT-Assisted Therapy in IVlaior Depressive Disorder Shows Consistent Quality of Psychedelic Response in Phase I", Feb. 22, 2022, https://www,biospace.comlarticietreleasesismall-pharma-inc-world-s-first-clinicai-trial-for-drnt-assisted-therapy-in-major-depressive-disorder-shows-consistent-duality-of-psychedelic-response-in-phase-Ds=67.

Cozzi et ai., "Synthe, sis and characterization of high-purity N,N-dimethyltryptamine hernifurnarate for human clinical trials", vol. 12, Issue 10, pp. 1483-1493, Jul. 2020, Drug Testing and Analysis.

Eaton et at, "Population-Based Study of First Onset and Chronicity in Major Depressive Disorder", vol. 65, Issue 5, pp. 513-520, May 2008, Archives of General Psychiatry.

Federal Register, "Requirements on Content and Format of Labeling for Human Prescription Drug and Biological Products", Jan. 24, 2006, https://web.archive.org/web/20170501143753/https://vmw.federalregist er.govidoc Li Ments/2006101/24106-545/reo u rements-on-content-and-format-of-labeling-for-human-prescription-drug-and-biologicai-products.

Kaplan et al., 't lood and urine levels of N,N-dimetnyitryptarnine following administration of psychoactive dosages to human subects vol. 38, issue 3, 1974, Psychopharmacologia.

Maicoim, Ben, "Can Psychedelics Heal Without Psychotherapy?", Oct. 4, 2019, https://web.archive.org/web1202109250644271https://www.spiritpharma cist. comiblogican-psychedelics-heal-without-psychotherapy.

National Institute of Mental Health, "Depression", Feb. 28, 2009, https://web.arch ive _.orglweb1202105312228591https://www.n im h. ni h .go/health/publications/depression/.

(Continued)

*Primary Examiner* — Timothy R Rozof

(74) *Attorney, Agent, or Firm* — Saul Ewing LLP; Kathryn Doyle; Domingos J. Silva

(57) ABSTRACT

Described herein is a method for treating, ameliorating, and/or preventing depression in a subject in need thereof. The method includes administering parenterally to the subject an effective amount of dimethyltryptamine (DMT) or a derivative thereof. Also described is a kit for performing methods described herein.

38 Claims, 29 Drawing Sheets

(56) References Cited

OTHER PUBLICATIONS

Kaplan et al., "Blood and urine levels of N,N-dimethyltryptamine following administration of psychoactive dosages to human subjects", vol. 38, Issue 3, 1974, Psychopharmacologia.†

Palhano-Fontez et al., "Rapid antidepressant effects of the psychedelic ayahuasca in treatment-resistant depression: a randomized placebo-controlled trial", vol. 49, pp. 655-663, Mar. 2019, Psychological Medicine.†

Eaton et al., "Population-Based Study of First Onset and Chronicity in Major Depressive Disorder", vol. 65, Issue 6, pp. 513-520, May 2008, Archives of General Psychiatry.†

Malcolm, Ben, "Can Psychedelics Heal Without Psychotherapy?", Oct. 4, 2019, https://web.archive.org/web/20210925064427/https://www.spiritpharmacist.com/blog/can-psychedelics-heal-without-psychotherapy.†

Federal Register, "Requirements on Content and Format of Labeling for Human Prescription Drug and Biological Products", Jan. 24, 2006, https://web.archive.org/web/20170501143763/https://www.federalregister.gov/documents/2006/01/24/06-545/requirements-on-content-and-format-of-labeling-for-human-prescription drug-and-biological-products.†

Arcee, "Mainlining into Peaceful Transcendence", Apr. 27, 2020, Erowid, https://erowid.org/experiences/exp.php?ID=101186.†

Small Pharma Ltd., "SPL026 (DMT Fumarate) in Healthy Subjects and MOD Patients", Dec. 17, 2020, Clinical Trials Registry, https://clinicaltrial v/study/NCT04673383.†

BioSpace, "Small Pharma Inc.: World's First Clinical Trial for DMT-Assisted Therapy in Major Depressive Disorder Shows Consistent Quality of Psychedelic Response in Phase I", Feb. 22, 2022 https://www.biospace.com/article/releases/small-pharma-inc-world-s-first-clinical-trial-for-dmt-assisted-therapy-in-major-depressive-disorder-shows-consistent-quality-of-psychedelic-response-in-phase-l/?s=67.†

Cozzi et al., "Synthesis and characterization of high-purity N,N-dimethyltryptamine hemifumarate for human clinical trials", vol. 12, Issue 10, pp. 1483-1493, Jul. 2020, Drug Testing and Analysis.†

Barker, Steven A., "N, N-Dimethyltryptamine (DMT), an Endogenous Hallucinogen: Past, Present, and Future Research to Determine Its Role and Function", vol. 12, pp. 1-17, Aug. 2018, Frontiers in Neuroscience.†

Zimmerman et al., "Severity classification on the Hamilton depression rating scale", vol. 150, Issue 2, pp. 384-388, Sep. 2014, Journal of Affective Disorders.†

Leucht et al., "Translating the HAM-D into the MADRS and vice versa with equipercentile linking", vol. 226, pp. 326-331, Jan. 2018, Journal of Affective Disorders.†

National Institute of Mental Health, "Depression", Feb. 28, 2009, https://web.archive.org/web/20210531222858/https://www.nimh.nih.gov/health/publications/depression/.†

* cited by examiner
† cited by third party

Table 1: Demographics

| | Group | Sex | Age, years | Race | Ethnic Origin | Employment status | Marital Status | Estimated illness duration, years | Baseline HAMD-17 total score | Baseline PHQ-9 | Past antidepressant trials | Past psychotherapy | Education | Weekly alcohol intake, units | Previous psychedelic use (time since last use) |
|---|---|---|---|---|---|---|---|---|---|---|---|---|---|---|---|
| 1 | HC | M | 58 | A | NH | E | M | N/A | N/A | N/A | N/A | N/A | >17 years | 7 | None |
| 2 | HC | M | 24 | A | NH | S | S | N/A | N/A | N/A | N/A | N/A | 17 years | 0 | Psilocybin (3 years ago) |
| 3 | HC | M | 24 | W | NH | E | DP | N/A | N/A | N/A | N/A | N/A | 16 years | 2 | None |
| 4 | MDD | F | 43 | W | NH | E | S | 22 | 22 | 22 | SSRI x 3<br>SNRI x 2<br>Atypical antidepressant x 1 | Yes | >17 years | 0 | MDMA (10+ years ago) |
| 5 | MDD | F | 59 | W | NH | U | M | 20+ | 25 | 22 | SSRI x 3<br>SNRI x 3<br>TCA x 2<br>Atypical antidepressant x 2 | Yes | >17 years | 0 | None |
| 6 | MDD | M | 31 | W | NH | E | M | 25 | 18 | 19 | SSRI x 1<br>Atypical antidepressant x 1 | Yes | >17 years | 0 | Psilocybin (6 weeks ago) |
| 7 | MDD | M | 59 | W | NH | E | M | 20+ | 28 | 14 | SSRI x 4<br>SNRI x 2<br>SGA x 1<br>Atypical antidepressant x 2<br>Mood stabilizer x 1 | Yes | >17 years | 0 | None |

Fig. 1A

| | | | | | | | | | | | | | | |
|---|---|---|---|---|---|---|---|---|---|---|---|---|---|---|
| | | | | | | | | | | | Ketamine x 1<br>ECT x 1 | | | | |
| 8 | MDD | F | 46 | W | NH | U | M | 20+ | 22 | 21 | SSRI x 2<br>Atypical antidepressant x1 | Yes | 16 years | 2 | Psilocybin (>20 years) |
| 9 | MDD | M | 38 | A | NH | E | S | 29 | 31 | 22 | SSRI x 5<br>TCA x 1<br>Atypical antidepressant x 2<br>Stimulant x 2<br>SGA x 4<br>Mood stabilizer x 2<br>Ketamine x 1<br>ECT x 1 | Yes | >17 years | 1 | Psilocybin (10 years) LSD (5 years) |
| 10 | MDD | M | 53 | W | NH | E | M | 20+ | 21 | 18 | SSRI x 3<br>SNRI x 1<br>Mood stabilizer x 2<br>Atypical antidepressant x 2 | Yes | 12 years | 0 | LSD (30 years) |

M: Male; F: female; W: white; A: asian; NH: nonhispanic; E: employed, UE: unemployed; S: student; M: married; S; single; DP; domestic partner; N/A: Not Applicable; HC: Healthy Control; MDD: Major Depressive Disorder; SSRI: Selective Serotonin Reuptake Inhibitor; SNRI: Serotonin Norepinephrine Reuptake Inhibitor; TCA: Tricyclic Antidepressant; ECT: Electro Convulsive Treatment; SGA: Second Generation Antipsychotic; LSD: Lysergic Acid Diethylamide

Fig. 1B

Table 2: Adverse Events

| Subject # | Group | DMT Dose | Adverse Event | Severity | Onset relative to DMT administration (minutes) | Duration | Comment |
|---|---|---|---|---|---|---|---|
| 1 | Healthy | 0.1 mg/kg | Headache | Mild | +45 | 5 hours | |
| | | 0.3 mg/kg | Hypertension | Moderate | +5 | 5 minutes | |
| 2 | | 0.1 mg/kg | - | - | - | - | |
| | | 0.3 mg/kg | Ringing sensation in the ears | Mild | +3 | 5 minutes | |
| 3 | | 0.1 mg/kg | Anxiety | Mild | -30 | 40 minutes | Anticipatory |
| | | | Lightheadedness | Mild | +1 | 10 minutes | |
| | | 0.3 mg/kg | Lightheadedness | Mild | +1 | 15 minutes | |
| | | | Tachycardia and subjective feeling of palpitation | Mild | +1 | 5 minutes | |
| 4 | Major Depressive Disorder | 0.1 mg/kg | Anxiety | Mild | 0 | 10 minutes | |
| | | 0.3 mg/kg | Back pain | Mild | The day after the test day, right after a moderately intense physical activity, improved with rest and pain killer use. | Significantly improved within 24 hours, completely subsided within a week. | History of back pain. |
| 5 | | 0.1 mg/kg | Headache | Mild | +1 | 20 seconds | |
| | | 0.3 mg/kg | Hypotension (asymptomatic). See supplement for details. | Severe** | +2 | 5 minutes | History of reflex syncope. |
| | | | Bradycardia (asymptomatic). See supplement for details. | Severe** | +2 | 5 minutes | History of reflex syncope. |
| 6 | | 0.1 mg/kg | Nausea | Mild | +4 | 5 minutes | |
| | | 0.3 mg/kg | Nausea | Mild | +2 | 5-10 minutes | |
| 7 | | 0.1 mg/kg | - | - | - | - | |

Fig. 3A

| | | | | | | | |
|---|---|---|---|---|---|---|---|
| | | 0.3 mg/kg | Anxiety | Mild | +2 | 60 minutes | |
| | | | Dysphoria | Mild | +5 | 24 hours | |
| 8 | | 0.1 mg/kg | Tingling | Mild | +3 | 15 minutes | |
| | | 0.3 mg/kg | - | - | - | - | |
| 9 | | 0.1 mg/kg | Anxiety | Mild | +2 | 30 minutes | |
| | | 0.3 mg/kg | Anxiety | Mild | -20 | 60 minutes | Anticipatory |
| 10 | | 0.1 mg/kg | Anxiety | Mild | -30 | 30 minutes | Anticipatory |
| | | | Hypertension | Mild | -30 | 20 minutes | |
| ** See S6 for details | | | | | | | |

Fig. 3B

Table 3: Dose-related Peak Change in Subjective Effects

| | | 0.1 mg/kg, mean (SD) | 0.3 mg/kg, mean (SD) | Statistic | Significance | Effect (Hedge's g) |
|---|---|---|---|---|---|---|
| **Psychedelic effects VAS** | Composite | 13.51 (11.75) | 53.46 (25.95) | $z = 4.05$ | $p < 0.0001$ | 2.20 |
| **PSI** | Total | 7.33(7.62) | 31.67(16.57) | $t = 4.84$ | $p = 0.001$ | 1.89 |
| **Depression and Anxiety VAS** | Anxiety | 2.56 (31.8) | 29.67 (39.96) | $z = 1.13$ | $p = 0.26$ | - |
| | Depression | 6.83 (28.9) | 14.83 (37.8) | $z = 0.11$ | $p = 0.92$ | - |

VAS: Visual Analog Scale; PSI: Psychotomimetic States Inventory

Fig. 4

| | p | Hedges g | 95% CI |
|---|---|---|---|
| 0.1 mg/kg vs. baseline | n.s | - | - |
| 0.3 mg/kg vs. baseline | 0.017 | 0.75 | (-7.80 to -1.2) |

Table S1: Schedule of Test Day

| Timepoint (minutes) | Procedures |
|---|---|
| -60 | Vital Signs<br>Baseline Ratings<br>Blood sampling<br>Scales: Psychedelic Effects VAS; PSI; VAS Anxiety and Depression (only for MDD) |
| -30 | Vital Signs |
| +0 | First DMT Dose (0.1 mg/kg)<br>Vital Signs |
| +5 | Vital Signs |
| +10 | Vital Signs |
| +15 | Vital Signs |
| +20 | Vital Signs |
| +30 | Vital Signs<br>Expected resolution of DMT acute effects<br>Blood sampling<br>Scales: Psychedelic Effects VAS; PSI; VAS Anxiety and Depression (only for MDD) |
| +45 | Vital Signs |
| +60 | Vital Signs; Continued observation |
| +120 | Vital Signs<br>Blood sampling<br>Scales: Psychedelic Effects VAS; PSI; VAS Anxiety and Depression (only for MDD); MMSE; Tolerability; Drug Liking Questionnaire<br>Determination to return for 0.3 mg/kg session (if applicable)<br>Discharge clearance |

VAS: Visual Analog Scale; PSI: Psychotomimetic States Inventory; MMSE: MiniMental State Examination

Fig. 6

| Signs and Symptoms of Serious Adverse Event | | | | | | |
|---|---|---|---|---|---|---|
| Time (mins) | Systolic mm Hg | Diastolic mm Hg | Heart rate bpm | O2 saturation | Symptoms | Comment |
| 0 | 108 | 60 | 54 | 100 | - | |
| +5 | 71 | 42 | 42 | 100 | *"nothing"* | The subject was asked how she was feeling. Vital signs monitoring increased to q 1 min. |
| +6 | 62 | 32 | 34 | 100 | - | IV opened up and head end of chair reclined around this time. |
| +7 | 56 | 30 | 32 | 100 | *"nothing"* | Asked her again how she was feeling, noting that oxygen saturation remained good. |
| +8 | 62 | 30 | 34 | 100 | - | |
| +9 | 77 | 48 | 42 | 100 | - | Noted that vital signs were increasing. |
| +10 | 97 | 62 | 46 | 100 | - | |
| +15 | 108 | 64 | 46 | 100 | *"I'm comfortable in this position"* (Trendelenberg) | |
| +20 | 110 | 70 | 60 | 100 | - | |

Mins: minutes, mm: millimeters, bpm: beats per minute, O2: oxygen

Fig. 8

Table S2: Dose Related Effects of DMT on Blood Pressure and Heart Rate

| | | 0 min | 5 min | 10 min | 15 min | 20 min | 30 min | 45 min | 60 min | 120 min | Effects | Post-Hoc: significant difference from baseline | Hedge's G (peak change) |
|---|---|---|---|---|---|---|---|---|---|---|---|---|---|
| Systolic mm Hg | 0.1mg/kg | 129 (11.2) | 144 (16.0) | 136 (11.4) | 136 (17.5) | 131 (11.6) | 131 (14.7) | 125 (11.7) | 123 (13.9) | 124 (10.3) | Time: F = 8.6 P = 0.001 Dose: F = 0.001 p = 0.98 Dose x time: F = 1.2 p = 0.36 | +5, +10, +15 (p ≤0 .01) | Time: 1.20 |
| | 0.3mg/kg | 124 (12.2) | 147 (37.6) | 141 (21.7) | 136 (14.9) | 131 (10.2) | 132 (11.8) | 130 (11.4) | 119 (9.4) | 120 (10.3) | | | Time: 0.90 |
| Diastolic mm Hg | 0.1mg/kg | 77 (5.7) | 84 (11.7) | 78 (9.5) | 79 (8.7) | 78 (6.9) | 79 (8.6) | 71 (6.9) | 72 (7.9) | 73 (6.5) | Time: F = 7.4; P < .001 Dose: F = 1.2; P = 0.49 Dose x time: F =0 .95, P = 0.34 | +5, +10, +15, +20, +30 (0.01 ≤ p ≤ 0.02) | Time: 0.85 |
| | 0.3mg/kg | 71 (6.3) | 80 (20.1) | 82 (10.4) | 80 (9.7) | 77 (8.4) | 80 (9.9) | 73 (10.1) | 70 (10.3) | 70 (9.4) | | | Time: 0.82 |
| | | | | | | | | | | | | | |
| Heart Rate bpm | 0.1mg/kg | 69 (8.2) | 75 (11.9) | 72 (11) | 69 (10.9) | 71 (11.3) | 70 (10.4) | 68 (12.1) | 68 (10.9) | 73 (6.5) | Time: F = 5.9 ; P = 0.008 Dose: F = 1.9; P = 0.19 Dose x time: F = 0.81; P = 0.38 | +5 (p = 0.002) | Time: 0.43 |
| | 0.3mg/kg | 81 (16.9) | 96 (18.1) | 76 (15.6) | 73 (15.8) | 72 (14.9) | 71 (15.9) | 71 (16.6) | 70 (14.2) | 70 (9.4) | | | Time: 0.86 |

Fig. 9

| Table S3: Dose-related Peak Change from Baseline in VAS Psychedelic Effects | | | | |
|---|---|---|---|---|
| Item | 0.1 mg/kg mean (SD) | 0.3 mg/kg mean (SD) | Statistic | Dose P-value |
| Intensity | 47.11(34.64) | 94.33(10.58) | 2.67 | 0.008** |
| Ego Disintegration | 11.00(22.81) | 68.11(36.05) | 2.52 | 0.012* |
| Saw geometric patterns | 37.78(41.16) | 81.56(30.64) | 1.90 | 0.058 |
| Elaborate/complex visual | 12.78(22.74) | 83.56(28.49) | 2.67 | 0.008** |
| Presence sentient life | 0.33(0.50) | 39.11(41.08) | 2.37 | 0.018* |
| Different reality | 3.56(7.75) | 69.11(29.89) | 2.67 | 0.008** |
| Felt more 'real' | 4.44(7.23) | 44.78(43.51) | 2.31 | 0.021* |
| Unusual bodily sensation | 29.33(29.82) | 34.56(22.22) | 0.53 | 0.59 |
| Things looked strange | 14.44(16.50) | 88.33(21.74) | 2.67 | 0.008** |
| Imagination vivid | 3.56(8.85) | 73.89(24.18) | 2.67 | 0.008** |
| Size/space alterations | 5.89(6.74) | 74.44(33.87) | 2.52 | 0.012* |
| Sounds influenced visual | 2.78(7.22) | 11.89(16.05) | 2.02 | 0.043 |
| Thoughts wandered freely | 13.11(25.07) | 39.00(40.47) | 1.69 | 0.091 |
| Sense time altered | 12.00(18.74) | 73.44(31.22) | 2.52 | 0.012* |
| Dreamlike quality | 11.89(11.71) | 67.78(29.35) | 2.67 | 0.008* |
| Sense of gratitude | 4.67(9.84) | 26.11(39.09) | 2.20 | 0.027* |
| Open/sensitive to all emotion | 14.11(28.63) | 36.67(33.09) | 2.52 | 0.012* |
| Displaced from body | 16.22(25.99) | 61.56(35.46) | 2.43 | 0.015 |
| pleasurable | 7.22(14.69) | 26.22(35.78) | 1.95 | 0.050 |
| Challenging | 25.00(32.48) | 65.89(31.96) | 2.31 | 0.021* |
| Meaningful | 8.22(17.09) | 45.78(39.59) | 2.67 | 0.008* |
| Buzzing sound at beginning | 4.11(8.46) | 22.11(36.98) | 1.52 | 0.13 |
| Felt normal | 21.11(27.69) | 1.44(2.92) | -1.3 | 0.19 |
| FDR correction ** p, adjusted < 0.01; *p, adjusted < 0.036 | | | | |

Fig. 10

Table S4: Dose-related Peak Change in Psychotomimetic Effects

| PSI subscales | 0.1 mg/kg DMT mean (SD) | 0.3 mg/kg DMT mean (SD) | P value | P, corrected** | Hedges' g |
|---|---|---|---|---|---|
| Thought distortion | 0.33 (0.71) | 1.89 (2.03) | 0.0312 | 0.16 | 1.02 |
| Perceptual disturbance | 4 (3.46) | 11 (4.61) | <0.001 | <0.005 | 1.71 |
| Cognitive disorganization | 2.11 (3.76) | 10.78 (7.12) | 0.010 | 0.05 | 1.52 |
| Anhedonia | 5 (2.74) | 4 (2.96) | 0.545 | 1.0 | 0.35 |
| Manic Experience | 0 (1) | 1.44 (2.92) | 0.172 | 0.86 | 0.66 |
| Paranoia | 0.33 (1.66) | 2.56 (3.05) | 0.0591 | 0.30 | 0.91 |

** Bonferroni correction by a factor of 5 (for 5 subscales)

Fig. 13

In-Session Anxiety and Depression (VAS)

| Table S5: Desirability of DMT | | | | |
|---|---|---|---|---|
| | Dose | Mean (SD) | Standardized Statistic | Significance (two-tailed) |
| How much are you willing to pay for the experience?<br>$ 0-100 | 0.1 mg/kg | 25.56 (29.07) | Z = -0.14 | P = 0.89 |
| | 0.3mg/kg | 24.78 (33.36) | | |
| How likely are you to use this drug?<br>0 (not at all) to 100 (most of all) | 0.1 mg/kg | 24.00 (17.91) | Z = -0.14 | P = 0.90 |
| | 0.3mg/kg | 22.44 (22.72) | | |

Fig. 16

Table S6: Change in Hamilton Depression Rating Scale (17 item) Scores Between the Baseline, 0.1 mg kg and 0.3 mg/kg DMT

| | Baseline (n=7) | 1 Day after 0.1 mg/kg of DMT (n=7) | 1 Day after 0.3 mg/kg of DMT (n=6)* |
|---|---|---|---|
| **Mean (SD)** | 23.86 (4.45) | 22.86 (3.85) | 19.83 (7.05) |
| **Difference versus baseline (95% CI)** | - | -1 (-2.07 to 0.07) | -4.5 (-7.80 to -1.2) |
| **SEM of differences** | - | 0.44 | 1.28 |
| **Hedges g value versus baseline** | - | 0.24 | 0.75 |
| **P value** | - | 0.062 | 0.017 |

HAMD was completed at baseline and 1 day after each test day. Effect sizes and P values reflect the results of a paired sample t test that compared scores between baseline and Day 1 after each test day.

*One subject was withdrawn administratively before completing the 2nd test day (0.3 mg.kg).

Fig. 17

METHOD OF TREATING AND AMELIORATING DEPRESSION

CROSS-REFERENCE TO RELATED APPLICATIONS

The present application claims priority under 35 U.S.C. § 119(e) to U.S. Provisional Patent Application No. 63/335,400, filed Apr. 27, 2022, which is incorporated herein by reference in its entirety.

BACKGROUND

Depressive disorders strongly affect quality of life, and are associated with considerable morbidity and mortality (Cuijpers et al., *Lancet Psychiatry*, Volume 7, Issue 11, November 2020, Pages 925-927). Depressive disorders affect a considerable percentage of the world population. For example, major depressive disorder (MDD) is estimated to affect about 2% of the world population (*Lancet.* 2018 Nov. 10; 392(10159): 1789-1858). Treatments available to depressive disorders include antidepressants and psychotherapy. However, such treatments sometimes work poorly or do not work at all. Therefore, there is a need for novel treatment methods for depression, especially novel treatment methods for treatment-resistant depression. The present invention addresses this need.

SUMMARY

In some aspects, the present invention is directed to the following non-limiting embodiments.

In some aspects, the present invention provides a method of treating, ameliorating, or preventing depression in a subject in need thereof, the method comprising: administering parenterally to the subject an effective amount of a dimethyltryptamine (DMT) compound, wherein the DMT compound is selected from the group consisting of DMT, a DMT salt, a DMT solvate, an isotopically labelled derivative of DMT, or any mixtures thereof.

In certain embodiments, the subject is administered the DMT compound intravenously.

In certain embodiments, the amount of the DMT compound administered to the subject ranges from about 0.038 mg/kg to about 0.38 mg/kg in terms of DMT content.

In certain embodiments, the subject is administered at least a first dose of an independently selected DMT compound and a second dose of an independently selected DMT compound, and wherein the dosage of the second dose in terms of DMT content is higher than the dosage of the first dose in terms of DMT content, wherein optionally the first dose and the second dose are at least 48 hours apart from each other.

In certain embodiments, the dosage of the first dose ranges from 0.038 mg/kg to 0.12 mg/kg of DMT content, and wherein the dosage of the second dose ranges from 0.15 mg/kg to 0.38 mg/kg in DMT content. In some embodiments, the dosage of the first dose or the second dose is calculated in terms of the DMT content in the DMT compound.

In certain embodiments, the subject is not administered a monoamine oxidase inhibitor (MAOI).

In certain embodiments, the DMT compound is administered as a pharmaceutical composition further comprising at least one pharmaceutically acceptable carrier.

In certain embodiments, the pharmaceutical composition does not comprise any other hallucinogenic or psychedelic agent besides the DMT compound.

In certain embodiments, the pharmaceutical composition does not comprise any other hallucinogenic or psychedelic agent besides the DMT compound in an amount sufficient to cause a measurable antidepressant, hallucinogenic, or psychedelic effect in the subject.

In certain embodiments, the pharmaceutical composition consists essentially of the DMT compound and at least one pharmaceutically acceptable carrier.

In certain embodiments, the DMT compound is N,N-dimethyltryptamine hemifumarate.

In certain embodiments, psychedelic effects experienced by the subject after the administration last for 60 minutes or less.

In certain embodiments, the depression is a major depressive disorder (MDD).

In certain embodiments, the Hamilton Rating Scale for Depression (HAMD-17) of the subject prior to the administration of the DMT or the salt, solvate, or isotopically labelled derivative thereof, or any mixture thereof, is 17 or higher.

In certain embodiments, the reduction of the HAMD-17 score of the subject is 3.0 points or more the day after the administration of the DMT compound.

In certain embodiments, the depression is treatment resistant or partially responsive.

In certain embodiments, the subject has suffered from the depression for 10 years or more prior to the administration of the DMT compound.

In certain embodiments, the subject is further administered a psychological distress medication or a hypertension medication.

In certain embodiments, the subject is not provided psychotherapy at the time of the administration of the DMT compound.

In certain embodiments, the peak serum level of DMT in the subject after the administration is lower than or equal to about 300 μg/dl, 290 μg/dl, 280 μg/dl, 270 μg/dl, 260 μg/dl, 250 μg/dl, 240 μg/dl, 230 μg/dl, 220 μg/dl, 210 μg/dl, 200 μg/dl, 190 μg/dl, 180 μg/dl, 170 μg/dl, 160 μg/dl, 150 μg/dl, 140 μg/dl, 130 μg/dl, 120 μg/dl, 110 μg/dl, 100 μg/dl, 90 μg/dl, 80 μg/dl, 70 μg/dl, 60 μg/dl, 50 μg/dl, 40 μg/dl, 30 μg/dl, 20 μg/dl, or 10 μg/dl in terms of DMT content.

In certain embodiments, the peak serum level of DMT in the subject after the administration is greater than or equal to about 290 μg/dl, 280 μg/dl, 270 μg/dl, 260 μg/dl, 250 μg/dl, 240 μg/dl, 230 μg/dl, 220 μg/dl, 210 μg/dl, 200 μg/dl, 190 μg/dl, 180 μg/dl, 170 μg/dl, 160 μg/dl, 150 μg/dl, 140 μg/dl, 130 μg/dl, 120 μg/dl, 110 μg/dl, 100 μg/dl, 90 μg/dl, 80 μg/dl, 70 μg/dl, 60 μg/dl, 50 μg/dl, 40 μg/dl, 30 μg/dl, 20 μg/dl, or 10 μg/dl in terms of DMT content.

In some aspects, the present invention provides a kit for treating, ameliorating, or preventing depression in a subject in need thereof, the kit comprising: a dimethyltryptamine (DMT) compound selected from the group consisting of DMT, a DMT salt, a DMT solvate, an isotopically labelled derivative of DMT, or any mixture thereof; and a manual instructing that the DMT compound is to be administered parenterally to the subject in an effective amount.

In certain embodiments, the manual instructs that the subject is to be administered with the DMT compound intravenously.

In certain embodiments, the manual instructs that the amount of the DMT compound to be administered to the subject ranges from about 0.038 mg/kg to about 0.38 mg/kg in terms of DMT content.

In certain embodiments, the manual instructs that the subject is to be administered with at least a first dose of an independently selected DMT compound and a second dose of an independently selected DMT compound, and wherein the dosage of the second dose in terms of DMT content is higher than the dosage of the first dose in terms of DMT content, wherein optionally the first dose and the second dose are at least 48 hours apart.

In certain embodiments, the dosage of the first dose ranges from 0.038 mg/kg to 0.12 mg/kg, and wherein the dosage of the second dose ranges from 0.15 mg/kg to 0.38 mg/kg. In some embodiments, the dosage of the first dose or the second dose is calculated by the DMT content in the DMT compound.

In certain embodiments, the DMT compound is not mixed with a monoamine oxidase inhibitor (MAOI).

In certain embodiments, the DMT compound is formulated as a pharmaceutical composition further comprising at least one pharmaceutically acceptable carrier.

In certain embodiments, the pharmaceutical composition does not comprise any other hallucinogenic or psychedelic agent besides the DMT compound.

In certain embodiments, the pharmaceutical composition does not comprise any other hallucinogenic or psychedelic agent besides the DMT compound in an amount sufficient to cause a measurable antidepressant, hallucinogenic, or psychedelic effect in the subject.

In certain embodiments, the pharmaceutical composition consists essentially of the DMT compound and at least one pharmaceutically acceptable carrier.

In certain embodiments, the DMT compound is N,N-dimethyltryptamine hemifumarate.

In certain embodiments, when the DMT compound is to be administered to the subject according to the instruction of the manual, psychedelic effects experienced by the subject after the administration last for 60 minutes or less.

In certain embodiments, the depression is a major depressive disorder (MDD).

In certain embodiments, the Hamilton Rating Scale for Depression (HAMD-17) of the subject prior to the administration of the DMT or the salt, solvate, or isotopically labelled derivative thereof, or any mixture thereof is 17 or higher.

In certain embodiments, when the DMT compound is administered to the subject according to the instruction of the manual, the HAMD-17 score of the subject is reduced by 3.0 points or more the day after the administration.

In certain embodiments, the depression is treatment resistant or partially responsive.

In certain embodiments, the subject has suffered from the depression for 10 years or more.

In certain embodiments, the kit further comprises a psychological distress medication or a hypertension medication.

In certain embodiments, the manual instructs that the subject does not need to be provided psychotherapy at the time of the administration of the DMT compound.

In certain embodiments, the peak serum level of DMT in the subject after the administration is lower than or equal to about 300 μg/dl, 290 μg/dl, 280 μg/dl, 270 μg/dl, 260 μg/dl, 250 μg/dl, 240 μg/dl, 230 μg/dl, 220 μg/dl, 210 μg/dl, 200 μg/dl, 190 μg/dl, 180 μg/dl, 170 μg/dl, 160 μg/dl, 150 μg/dl, 140 μg/dl, 130 μg/dl, 120 μg/dl, 110 μg/dl, 100 μg/dl, 90 μg/dl, 80 μg/dl, 70 μg/dl, 60 μg/dl, 50 μg/dl, 40 μg/dl, 30 μg/dl, 20 μg/dl, or 10 μg/dl in terms of DMT content.

In certain embodiments, the peak serum level of DMT in the subject after the administration is greater than or equal to about 290 μg/dl, 280 μg/dl, 270 μg/dl, 260 μg/dl, 250 μg/dl, 240 μg/dl, 230 μg/dl, 220 μg/dl, 210 μg/dl, 200 μg/dl, 190 μg/dl, 180 μg/dl, 170 μg/dl, 160 μg/dl, 150 μg/dl, 140 μg/dl, 130 μg/dl, 120 μg/dl, 110 μg/dl, 100 μg/dl, 90 μg/dl, 80 μg/dl, 70 μg/dl, 60 μg/dl, 50 μg/dl, 40 μg/dl, 30 μg/dl, 20 μg/dl, or 10 μg/dl in terms of DMT content.

BRIEF DESCRIPTION OF THE DRAWINGS

The following detailed description of exemplary embodiments will be better understood when read in conjunction with the appended drawings. For the purpose of illustrating, non-limiting embodiments are shown in the drawings. It should be understood, however, that the instant specification is not limited to the precise arrangements and instrumentalities of the embodiments shown in the drawings.

FIGS. 1A-1B describe certain aspects of the clinical trial participants' demographic and clinical characteristics, in accordance with some embodiments.

FIG. 2A: systolic blood pressure (mm Hg). FIG. 2B: diastolic blood pressure (mm Hg). FIG. 2C: heart rate (beats/minute). Arrows indicate the time at which DMT was administered. n=10 for 0.1 mg/kg (n=3 healthy, n=7 depressed) and n=9 for 0.3 mg/kg (n=3 healthy, n=6 depressed).

FIGS. 3A-3B describe adverse events experienced by the clinical trial participants, in accordance with some embodiments.

FIG. 4 describes certain aspects of the dose-related peak change in subjective effects, in accordance with some embodiments.

FIG. 5 shows changes in HamD-17 total scores of individual participants the day after 0.1 mg/kg and 0.3 mg/kg DMT relative to baseline. Each subject is represented by one line. The group mean is also shown. *Note that subject #7 completed the 0.1 mg/kg dosing session before being withdrawn for administrative reasons.

FIG. 6 describes the schedule of the test day, in accordance with some embodiments.

FIG. 7 shows changes in individual ratings of overall tolerability on the 0.1 mg/kg and 0.3 mg/kg DMT scored on a scale of 0=intolerable to 100=well-tolerated. Overall tolerability of the test day was scored at the end of each test day when there were no lingering effects. Subjects 1-3 are healthy volunteers and subjects 4-10 are individuals with major depressive disorder. The far right indicated the group mean of each dose.

FIG. 8 describes the signs and symptoms of serious adverse event, in accordance with some embodiments.

FIG. 9 describes the dose related effects of DMT on blood pressure and heart rate, in accordance with some embodiments.

FIG. 10 describes the dose-related peak change from baseline in VAS psychedelic effects, in accordance with some embodiments.

FIG. 13 describes the dose-related peak change in psychotomimetic effects, in accordance with some embodiments.

FIG. 16 describes the desirability of DMT, in accordance with some embodiments.

FIG. 17 describes the change in Hamilton Depression Rating Scale (17 item) scores between the baseline, 0.1 mg/kg, and 0.3 mg/kg DMT.

DETAILED DESCRIPTION

Figure 2A:
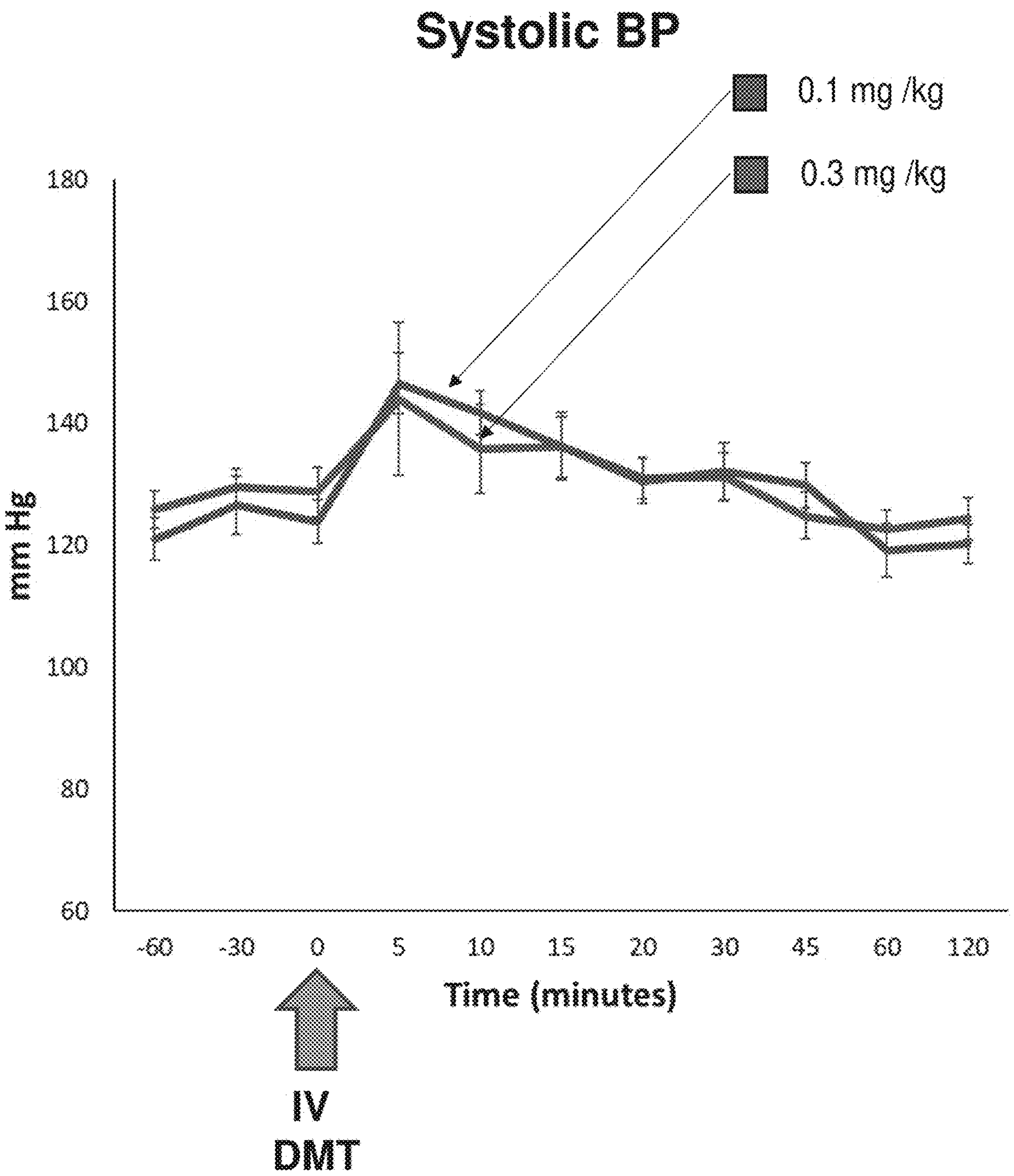
FIGS. 2A-2C depict the blood pressure and heart rate changes in means (error bars indicate standard error of mean) over time on the 0.1 mg/kg and 0.3 mg/kg DMT, in accordance with some embodiments.

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

Orally administrations of serotonergic psychedelics (also referred to as serotonergic hallucinogens) such as psilocybin and lysergic acid diethylamide (LSD) have been applied in the treatment of neuropsychiatric disorders such as major depressive disorder, and are considered effective.

However, these compounds cause acute psychedelic effects in the patients, which take time to emerge, last for several hours and whose magnitude and duration cannot be changed once administered. The psychedelic effects are sometimes negative and the patients can become anxious with the acute psychedelic effect and have a "bad trip." As a result, in the existing model two therapists are required to be present for the entire dosing session to facilitate psychotherapy and to attend to participants who have a bad trip.

The study described herein ("the present study") evaluated the parental (such as intravenous) administration of dimethyltryptamine (DMT) to treat depression, and confirmed the effectiveness. Notably, the present study discovered that, in contrast to the conventional orally administered psilocybin and LSD, intravenously administered dimethyltryptamine (DMT) allows for near instantaneous acute psychedelic effects which last for only 20-30 minutes. Due to the quick onset and short duration of the psychedelic effects, even if the patient experiences a "bad trip," managing the psychedelic effects are much easier. Furthermore, the results show that the intravenous DMT administration was well tolerated by both MDD patients and HC individuals and suggested that intravenous DMT has low abuse potential.

Accordingly, in some embodiments, the present invention is directed to a method of treating, ameliorating, and/or preventing depression in a subject in need thereof.

In some embodiments, the present invention is directed to a kit for treating, ameliorating and/or preventing depression in a subject in need thereof.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, peptide chemistry, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

"About" as used herein when referring to a measurable value such as an amount, a temporal duration, and the like, is meant to encompass variations of 20% or ±10%, in certain embodiments ±5%, in certain embodiments ±1%, in certain embodiments ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

In one aspect, the terms "co-administered" and "co-administration" as relating to a subject refer to administering to the subject a compound and/or composition of the disclosure along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, "DMT" refers to N,N-dimethyltryptamine, which has the molecular formula $C_{12}H_{16}N_2$ and molecular weight of 188.274 g/mole:

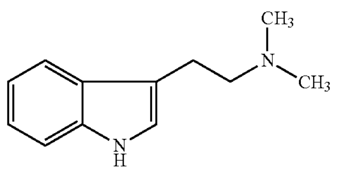

As used herein, the "DMT content" of a DMT compound corresponds to the amount of DMT itself contained in a certain amount of the DMT compound. The DMT content can be expressed in any units used in pharmacology and/or chemistry, such as %, material mass, material mass per body mass, and so forth.

As used herein, "DMT hemifumarate" corresponds to the DMT compound:

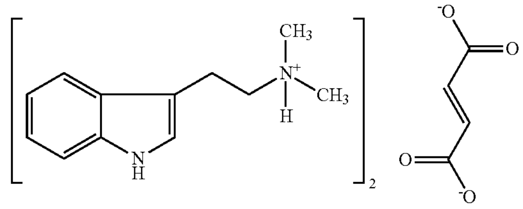

The DMT hemifumarate has a formula of $2(C_{12}H_{16}N_2)\cdot$(HOOC—CH═CH—COOH) and molecular weight of 492.61 g/mole. It follows that the DMT content in DMT hemifumarate is [2×188.27/492.61]=76.4%. For example, 1 g of DMT hemifumarate corresponds 0.764 g of DMT (also referred to as in DMT content), and 0.05 mg/kg of DMT hemifumarate corresponds to 0.038 mg/kg of DMT (also referred to as in DMT content), and so forth.

As used herein, the term "pharmaceutical composition" or "composition" refers to a mixture of at least one compound useful within the disclosure with a pharmaceutically acceptable carrier. The pharmaceutical composition facilitates administration of the compound to a patient. Multiple techniques of administering a compound exist in the art including, but not limited to, subcutaneous, intravenous, oral, aerosol, inhalational, rectal, vaginal, transdermal, intranasal, buccal, sublingual, parenteral, intrathecal, intragastrical, ophthalmic, pulmonary, and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the disclosure within or to the patient such that it may perform its intended function. Each carrier must be "acceptable" in the sense of being compatible with the other ingredients of the formulation, including the compound useful within the disclosure, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the disclosure, and are physiologically acceptable to the patient. The "pharmaceutically acceptable carrier" may further include a pharmaceutically acceptable salt of the compound useful within the disclosure. Other additional ingredients that may be included in the pharmaceutical compositions used in the practice of the disclosure are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein, a "pharmaceutically effective amount," "therapeutically effective amount," or "effective amount" of a compound is that amount of compound that is sufficient to provide a beneficial effect to the subject to which the compound is administered.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, a "psychedelic effect" associated to a drug refers to any measurable change in a subject's mood, thoughts, sense of self, consciousness, and/or perceptions (such as, but not limited to hallucinations, illusions) due to administration of the drug.

As used herein, the terms "subject" and "individual" and "patient" can be used interchangeably and may refer to a human or non-human mammal or a bird. Non-human mammals include, for example, livestock and pets, such as ovine, bovine, porcine, canine, feline and murine mammals. In certain embodiments, the subject is human.

As used herein, the term "treatment" or "treating" is defined as the application or administration of a therapeutic agent, i.e., a compound useful within the disclosure (alone or in combination with another pharmaceutical agent), to a patient, or application or administration of a therapeutic agent to an isolated tissue or cell line from a patient (e.g., for diagnosis or ex vivo applications), who has a disease or disorder and/or a symptom of a disease or disorder, with the purpose to cure, heal, alleviate, relieve, alter, remedy, ameliorate, improve or affect the disease or disorder and/or the symptoms of the disease or disorder. Such treatments may be specifically tailored or modified, based on knowledge obtained from the field of pharmacogenomics.

Method of Treating, Ameliorating and/or Preventing Depression

In some aspects, the present invention is directed to a method of treating, ameliorating, and/or preventing depression in a subject in need thereof. In some embodiments, the subject is a human subject.

In some embodiments, the method includes administering parenterally to the subject an effective amount of dimethyltryptamine (DMT), or a salt, solvate, or isotopically labelled derivative thereof, or any mixture thereof.

In certain embodiments, the DMT or the salt, solvate, or isotopically labelled derivative thereof, or any mixture thereof, is referred to as the DMT compound.

In some embodiments, the DMT or the salt, solvate, or isotopically labelled derivative thereof, or any mixture thereof is administered intravenously to the subject.

The present study has realized that, when administered orally, psychedelic compounds cause prolonged psychedelic effects which can sometimes last for about 4 hours to 6 hours, and the onset of the psychedelic effects are sometimes delayed. Since patients having a psychedelic experience requires at least some degrees of care from medical practitioners, especially if the psychedelic experience is negative (e.g., "bad trips"), these long and delayed psychedelic effects are considered highly undesirable. The present study confirmed that the parental administration, such as intravenous administration, of a non-limiting exemplary DMT salt (water-soluble N,N-dimethyltryptamine hemifumarate) resulted in quick and short psychedelic effects which are easily manageable.

In some embodiments, the amount of the DMT or the salt, solvate, or isotopically labelled derivative thereof, or any mixture thereof administered to the subject ranges from about 0.038 mg/kg to about 0.38 mg/kg in terms of DMT content, such as about 0.057 mg/kg to about 0.31 mg/kg or about 0.076 mg/kg to about 0.23 mg/kg in terms of DMT content.

In some embodiments, the amount of the DMT or the salt, solvate, or isotopically labelled derivative thereof, or any mixture thereof administered to the subject is equal to or greater than about 0.038, 0.040, 0.042, 0.044, 0.046, 0.048, 0.050, 0.052, 0.054, 0.056, 0.058, 0.060, 0.062, 0.064, 0.066, 0.068, 0.070, 0.072, 0.074, 0.076, 0.078, 0.040, 0.042, 0.044, 0.046, 0.048, 0.05, 0.052, 0.054, 0.056, 0.058, 0.06, 0.062, 0.064, 0.066, 0.068, 0.07, 0.072, 0.074, 0.076, 0.078, 0.08, 0.082, 0.084, 0.086, 0.088, 0.09, 0.092, 0.094, 0.096, 0.098, 0.1, 0.102, 0.104, 0.106, 0.108, 0.11, 0.112, 0.114, 0.116, 0.118, 0.12, 0.122, 0.124, 0.126, 0.128, 0.13, 0.132, 0.134, 0.136, 0.138, 0.14, 0.142, 0.144, 0.146, 0.148, 0.15, 0.152, 0.154, 0.156, 0.158, 0.16, 0.162, 0.164, 0.166, 0.168, 0.17, 0.172, 0.174, 0.176, 0.178, 0.18, 0.182, 0.184, 0.186, 0.188, 0.19, 0.192, 0.194, 0.196, 0.198, 0.2, 0.202, 0.204, 0.206, 0.208, 0.21, 0.212, 0.214, 0.216, 0.218, 0.22, 0.222, 0.224, 0.226, 0.228, 0.23, 0.232, 0.234, 0.236, 0.238, 0.24, 0.242, 0.244, 0.246, 0.248, 0.25, 0.252, 0.254, 0.256, 0.258, 0.26, 0.262, 0.264, 0.266, 0.268, 0.27, 0.272, 0.274, 0.276, 0.278, 0.28, 0.282, 0.284, 0.286, 0.288, 0.29, 0.292, 0.294, 0.296, 0.298, 0.3, 0.302, 0.304, 0.306, 0.308, 0.31, 0.312, 0.314, 0.316, 0.318, 0.32, 0.322, 0.324, 0.326, 0.328, 0.33, 0.332, 0.334, 0.336, 0.338, 0.34, 0.342, 0.344, 0.346, 0.348, 0.35, 0.352, 0.354, 0.356, 0.358, 0.36, 0.362, 0.364, 0.366, 0.368, 0.37, 0.372, 0.374, 0.376, 0.378, 0.38, or 0.40 mg/kg in terms of DMT content.

In some embodiments, the amount of the DMT or the salt, solvate, or isotopically labelled derivative thereof, or any mixture thereof administered to the subject is equal to or less than about 0.038, 0.040, 0.042, 0.044, 0.046, 0.048, 0.050, 0.052, 0.054, 0.056, 0.058, 0.060, 0.062, 0.064, 0.066, 0.068, 0.070, 0.072, 0.074, 0.076, 0.078, 0.040, 0.042, 0.044, 0.046, 0.048, 0.05, 0.052, 0.054, 0.056, 0.058, 0.06, 0.062, 0.064, 0.066, 0.068, 0.07, 0.072, 0.074, 0.076, 0.078, 0.08, 0.082, 0.084, 0.086, 0.088, 0.09, 0.092, 0.094, 0.096, 0.098, 0.1, 0.102, 0.104, 0.106, 0.108, 0.11, 0.112, 0.114, 0.116, 0.118, 0.12, 0.122, 0.124, 0.126, 0.128, 0.13, 0.132, 0.134, 0.136, 0.138, 0.14, 0.142, 0.144, 0.146, 0.148, 0.15, 0.152, 0.154, 0.156, 0.158, 0.16, 0.162, 0.164, 0.166, 0.168, 0.17, 0.172, 0.174, 0.176, 0.178, 0.18, 0.182, 0.184, 0.186, 0.188, 0.19, 0.192, 0.194, 0.196, 0.198, 0.2, 0.202, 0.204, 0.206, 0.208, 0.21, 0.212, 0.214, 0.216, 0.218, 0.22, 0.222, 0.224, 0.226, 0.228, 0.23, 0.232, 0.234, 0.236, 0.238, 0.24, 0.242, 0.244, 0.246, 0.248, 0.25, 0.252, 0.254, 0.256, 0.258, 0.26, 0.262, 0.264, 0.266, 0.268, 0.27, 0.272, 0.274, 0.276, 0.278, 0.28, 0.282, 0.284, 0.286, 0.288, 0.29, 0.292, 0.294, 0.296, 0.298, 0.3, 0.302, 0.304, 0.306, 0.308, 0.31, 0.312, 0.314, 0.316, 0.318, 0.32, 0.322, 0.324, 0.326, 0.328, 0.33, 0.332, 0.334, 0.336, 0.338, 0.34, 0.342, 0.344, 0.346, 0.348, 0.35, 0.352, 0.354, 0.356, 0.358, 0.36, 0.362, 0.364, 0.366, 0.368, 0.37, 0.372, 0.374, 0.376, 0.378, 0.38, or 0.40 mg/kg in terms of DMT content.

In some embodiments, the subject is administered with at least a first dose and a second dose of the DMT or the salt, solvate, or isotopically labelled derivative thereof, or any mixture thereof. In some embodiments, a dosage of the second dose in terms of DMT content is higher than a dosage of the first dose in terms of DMT content. In some embodiments, the dosage of the first dose ranges from about 0.038 mg/kg to about 0.12 mg/kg in terms of DMT content, such as from about 0.057 mg/kg to about 0.096 mg/kg or about 0.076 mg/kg in terms of DMT content. In some embodiments, the dosage of the second dose ranges from about 0.15 mg/kg to about 0.38 mg/kg in terms of DMT content, such as from about 0.19 mg/kg to about 0.31 mg/kg or about 0.23 mg/kg in terms of DMT content.

In some embodiments, the dosage of the first dose is equal to or greater than about 0.038, 0.040, 0.042, 0.044, 0.046, 0.048, 0.050, 0.052, 0.054, 0.056, 0.058, 0.060, 0.062, 0.064, 0.066, 0.068, 0.070, 0.072, 0.074, 0.076, 0.078, 0.040, 0.042, 0.044, 0.046, 0.048, 0.05, 0.052, 0.054, 0.056, 0.058, 0.06, 0.062, 0.064, 0.066, 0.068, 0.07, 0.072, 0.074, 0.076, 0.078, 0.08, 0.082, 0.084, 0.086, 0.088, 0.09, 0.092, 0.094, 0.096, 0.098, 0.1, 0.102, 0.104, 0.106, 0.108, 0.11, 0.112, 0.114, 0.116, 0.118, or 0.12 mg/kg in terms of DMT content.

In some embodiments, the dosage of the first dose is equal to or less than about 0.038, 0.040, 0.042, 0.044, 0.046, 0.048, 0.050, 0.052, 0.054, 0.056, 0.058, 0.060, 0.062, 0.064, 0.066, 0.068, 0.070, 0.072, 0.074, 0.076, 0.078, 0.040, 0.042, 0.044, 0.046, 0.048, 0.05, 0.052, 0.054, 0.056, 0.058, 0.06, 0.062, 0.064, 0.066, 0.068, 0.07, 0.072, 0.074, 0.076, 0.078, 0.08, 0.082, 0.084, 0.086, 0.088, 0.09, 0.092, 0.094, 0.096, 0.098, 0.1, 0.102, 0.104, 0.106, 0.108, 0.11, 0.112, 0.114, 0.116, 0.118, or 0.12 mg/kg in terms of DMT content.

In some embodiments, the dosage of the second dose is equal to or greater than about 0.15, 0.152, 0.154, 0.156, 0.158, 0.16, 0.162, 0.164, 0.166, 0.168, 0.17, 0.172, 0.174, 0.176, 0.178, 0.18, 0.182, 0.184, 0.186, 0.188, 0.19, 0.192, 0.194, 0.196, 0.198, 0.2, 0.202, 0.204, 0.206, 0.208, 0.21, 0.212, 0.214, 0.216, 0.218, 0.22, 0.222, 0.224, 0.226, 0.228, 0.23, 0.232, 0.234, 0.236, 0.238, 0.24, 0.242, 0.244, 0.246, 0.248, 0.25, 0.252, 0.254, 0.256, 0.258, 0.26, 0.262, 0.264, 0.266, 0.268, 0.27, 0.272, 0.274, 0.276, 0.278, 0.28, 0.282, 0.284, 0.286, 0.288, 0.29, 0.292, 0.294, 0.296, 0.298, 0.3, 0.302, 0.304, 0.306, 0.308, 0.31, 0.312, 0.314, 0.316, 0.318, 0.32, 0.322, 0.324, 0.326, 0.328, 0.33, 0.332, 0.334, 0.336, 0.338, 0.34, 0.342, 0.344, 0.346, 0.348, 0.35, 0.352, 0.354, 0.356, 0.358, 0.36, 0.362, 0.364, 0.366, 0.368, 0.37, 0.372, 0.374, 0.376, 0.378, 0.38, or 0.40 mg/kg in terms of DMT content.

In some embodiments, the dosage of the second dose is equal to or less than about 0.15, 0.152, 0.154, 0.156, 0.158, 0.16, 0.162, 0.164, 0.166, 0.168, 0.17, 0.172, 0.174, 0.176, 0.178, 0.18, 0.182, 0.184, 0.186, 0.188, 0.19, 0.192, 0.194, 0.196, 0.198, 0.2, 0.202, 0.204, 0.206, 0.208, 0.21, 0.212, 0.214, 0.216, 0.218, 0.22, 0.222, 0.224, 0.226, 0.228, 0.23, 0.232, 0.234, 0.236, 0.238, 0.24, 0.242, 0.244, 0.246, 0.248, 0.25, 0.252, 0.254, 0.256, 0.258, 0.26, 0.262, 0.264, 0.266, 0.268, 0.27, 0.272, 0.274, 0.276, 0.278, 0.28, 0.282, 0.284, 0.286, 0.288, 0.29, 0.292, 0.294, 0.296, 0.298, 0.3, 0.302, 0.304, 0.306, 0.308, 0.31, 0.312, 0.314, 0.316, 0.318, 0.32, 0.322, 0.324, 0.326, 0.328, 0.33, 0.332, 0.334, 0.336, 0.338, 0.34, 0.342, 0.344, 0.346, 0.348, 0.35, 0.352, 0.354, 0.356, 0.358, 0.36, 0.362, 0.364, 0.366, 0.368, 0.37, 0.372, 0.374, 0.376, 0.378, 0.38, or 0.40 mg/kg in terms of DMT content.

In some embodiments, the first dose and the second dose are at least 24 hours apart, such as equal to or greater than 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, or 72 hours apart.

In some embodiments, the subject is not administered with a monoamine oxidase inhibitor (MAOI), such as harmaline. The plant ayahuasca contains both DMT and MAOIs.

In some embodiments, the DMT or the salt, solvate, or isotopically labelled derivative thereof to be administered to the subject is substantially pure. As used herein, the term "substantially pure," when referring to the DMT or the derivatives thereof, means that the DMT or the derivatives thereof are not substantially mixed with other pharmaceutically effective agents (such as but not limited to psychedelic agents) and/or include substantial amount of impurities associated with the DMT or the derivatives thereof if they are, for example, extracted from natural sources, such as ayahuasca.

In certain embodiments, the DMT or the salt, solvate, or isotopically labelled derivative thereof is formulated as a pharmaceutical composition further comprising at least one pharmaceutically acceptable carrier.

In certain embodiments, the pharmaceutical composition does not comprise any other hallucinogenic or psychedelic agent besides the DMT compound.

In certain embodiments, the pharmaceutical composition does not comprise any other hallucinogenic or psychedelic agent besides the DMT compound in an amount sufficient to cause a measurable antidepressive, hallucinogenic, or psychedelic effect in the subject.

In certain embodiments, the pharmaceutical composition consists essentially of the DMT compound and at least one pharmaceutically acceptable carrier.

In certain embodiments, the pharmaceutical composition consists of the DMT compound and at least one pharmaceutically acceptable carrier.

In some embodiments, the subject is administered with the salt of DMT, and wherein the salt of DMT (or DMT compound) is N,N-dimethyltryptamine hemifumarate.

In some embodiments, psychedelic effects experienced by the subject after the administration last for about 60 minutes or less, such as about 50 minutes or less, about 40 minutes or less, or about 30 minutes or less.

In some embodiments, the onset of the psychedelic effects after the administration is within about 15 minutes or less, about 10 minutes or less, or about 5 minutes or less.

In some embodiments, the depression is a major depressive disorder (MDD).

In some embodiments the Hamilton Rating Scale for Depression (HAMD-17) of the subject prior to the administration of the DMT or the salt, solvate, or isotopically labelled derivative thereof, or any mixture thereof is 17 or higher, such as 24 or higher.

In some embodiments, the reduction of the HAMD-17 score of the subject is 3.0 points or more, such as 3.5 points or more, 4.0 points or more or 4.5 points or more the day after the administration of the DMT or the salt, solvate, or isotopically labelled derivative thereof, or any mixture thereof.

In some embodiments, the depression is treatment resistant. The definition of treatment-resistant depression can be found in, for example, Gaynes et al. (*Depression and anxiety.* 2020; 37(2):134-45). The entirety of the reference is hereby incorporated herein by reference. Briefly, treatment resistant as defined as a minimum of two prior treatment failures and confirmation of prior adequate dose and duration, and at least one failed antidepressant trial in the current depressive episode. In some embodiments, the depression is partially responsive.

In some embodiments, prior to administering the DMT or the salt, solvate, or isotopically labelled derivative thereof, or any mixture thereof according to the method herein, the subject has suffered from the depression for 10 years or more, such as 12 years or more or 15 years or more.

In some embodiments, the subject is further administered with a psychological distress medication, such as lorazepam and risperidone. In some embodiments, the psychological distress medication is administered to manage the psychedelic effects, especially the negative psychedelic effects, caused by the DMT or the derivatives thereof. In some embodiments, the subject is further administered with a hypertension medication, such as labetalol. In some embodiments, the hypertension medication is administered to manage the increased blood pressures and heart rates caused by the DMT compound.

In some embodiments, the subject is not given psychotherapy at the time of the administration of the DMT or the salt, solvate, or isotopically labelled derivative thereof, or any mixture thereof. As used herein, the term "not given psychotherapy" does not mean that psychotherapies should be purposely avoided. One of ordinary skill in the art would understand that psychedelic medications are typically administered in settings adorned with art, plants, flowers, and homey furnishings, painted in warm colors, and lit with muted lighting, which are considered a form of psychotherapy. These settings do not have to be removed if readily available. Rather, "not given psychotherapy" means that the method herein can be performed in regular hospital settings.

In certain embodiments, the peak serum level of DMT in the subject after the administration is lower than or equal to about 300 μg/dl, 290 μg/dl, 280 μg/dl, 270 μg/dl, 260 μg/dl, 250 μg/dl, 240 μg/dl, 230 μg/dl, 220 μg/dl, 210 μg/dl, 200 μg/dl, 190 μg/dl, 180 μg/dl, 170 μg/dl, 160 μg/dl, 150 μg/dl, 140 μg/dl, 130 μg/dl, 120 μg/dl, 110 μg/dl, 100 μg/dl, 90 μg/dl, 80 μg/dl, 70 μg/dl, 60 μg/dl, 50 μg/dl, 40 μg/dl, 30 μg/dl, 20 μg/dl, or 10 μg/dl in terms of DMT content.

In certain embodiments, the peak serum level of DMT in the subject after the administration is greater than or equal to about 290 μg/dl, 280 μg/dl, 270 μg/dl, 260 μg/dl, 250 μg/dl, 240 μg/dl, 230 μg/dl, 220 μg/dl, 210 μg/dl, 200 μg/dl, 190 μg/dl, 180 μg/dl, 170 μg/dl, 160 μg/dl, 150 μg/dl, 140 μg/dl, 130 μg/dl, 120 μg/dl, 110 μg/dl, 100 μg/dl, 90 μg/dl, 80 μg/dl, 70 μg/dl, 60 μg/dl, 50 μg/dl, 40 μg/dl, 30 μg/dl, 20 μg/dl, or 10 μg/dl in terms of DMT content.

Figure 19A:
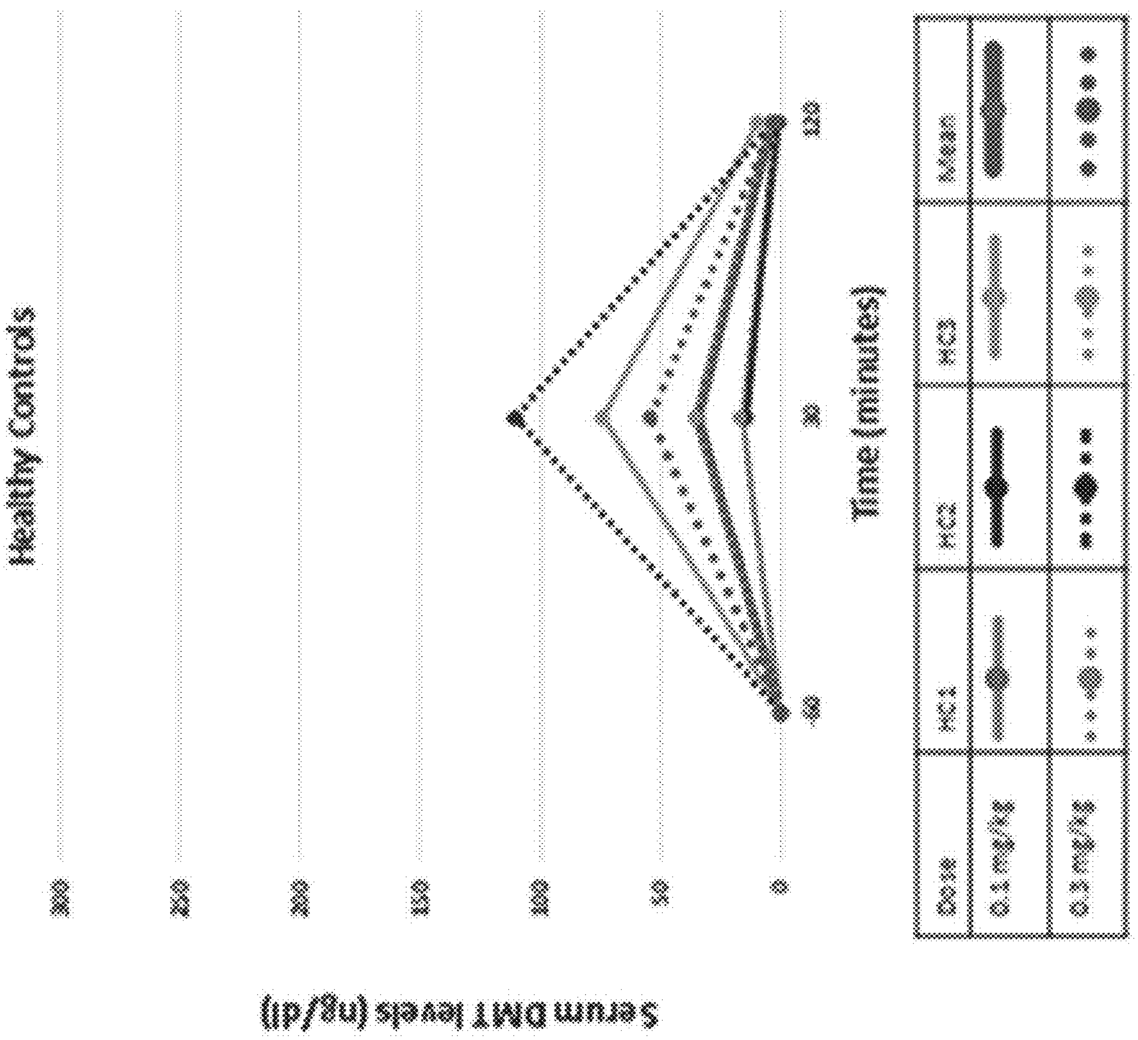
FIGS. 19A-19B depict serum DMT levels in healthy control (FIG. 19A) and depression subjects (FIG. 19B) with intravenous administration of DMT hemifumarate, in accordance with some embodiments. Y-axis: serum DMT levels (ng/dl); X-axis: 60 min before DMT administration; and 30 and 60 min after DMT administration. Each subject's levels at each dose are displayed separately. Solid line (0.1 mg/kg) and dotted line (0.3 mg/kg). Mean of the group at each dose is also displayed.
Figure 19B:
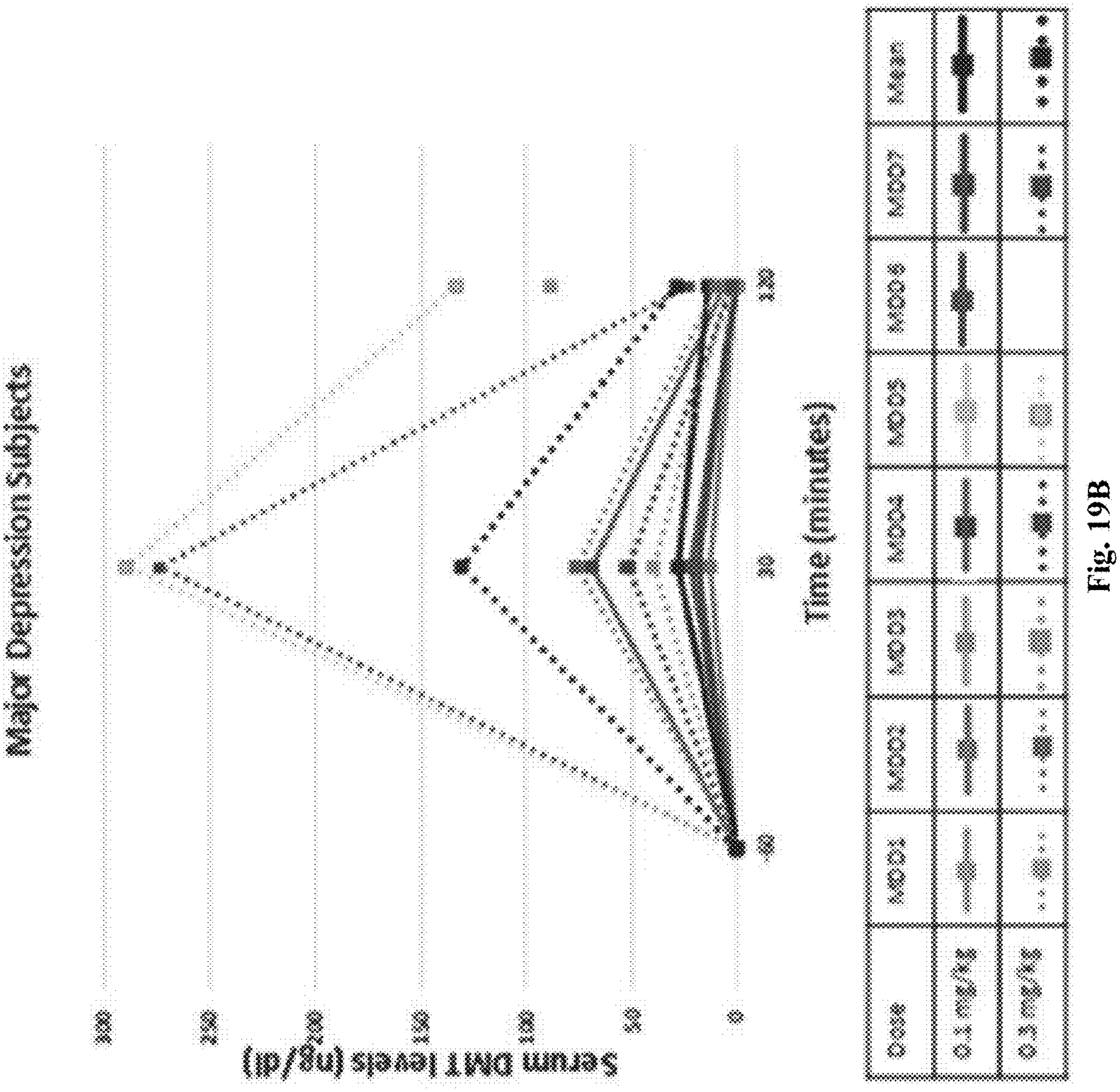

The present study observed that the bodies of depression patients sometimes process DMT differently from healthy subjects and can have higher serum DMT levels in comparison with the healthy subjects when the same amount of DMT compounds were administered (see e.g., FIGS. 19A-19B). As such, in some embodiments, the method further includes administering to the patients a test dose of DMT compound, and determine a DMT level in the serum of the patient in one or more time points post administration to establish a personalized DMT pharmacokinetics profile, such as serum DMT level profile.

Kit for Treating, Ameliorating, and/or Preventing Depression

In some aspects, the present invention is directed to a kit for treating, ameliorating and/or preventing depression in a subject in need thereof. In some embodiments, the subject is a human subject.

In some embodiments, the kit includes dimethyltryptamine (DMT), or a salt, solvate, or isotopically labelled derivative thereof, or any mixture thereof, and a manual instructing to perform the method herein, such as the method detailed in the "Method of Treating, Ameliorating and/or Preventing Depression" section.

In some embodiments, the kit further includes a medication for psychological distress, such as lorazepam and risperidone or a medication for hypertension, as the method herein sometimes require these medications.

Combination Therapies

In some embodiments, the method of treating, ameliorating, and/or preventing the depressive disorder or includes administering to the subject the effective amount of at least one compound and/or composition contemplated within the disclosure.

In some embodiments, the composition for treating, ameliorating, and/or preventing depressive disorder includes at least one compound and/or composition contemplated within the disclosure.

In some embodiments, the subject is further administered at least one additional agent that treats, ameliorates, and/or prevents a depressive disorder. In other embodiments, the compound and the at least one additional agent are co-administered to the subject. In yet other embodiments, the compound and the at least one additional agent are co-formulated.

The compounds contemplated within the disclosure are intended to be useful in combination with one or more additional compounds. These additional compounds may comprise compounds of the present disclosure and/or at least one additional agent for treating depressive disorders, and/or at least one additional agent that treats one or more diseases or disorders contemplated herein.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations contemplated within the disclosure may be administered to the subject either prior to or after the onset of a disease and/or disorder contemplated herein. Further, several divided dosages, as well as staggered dosages may be administered daily or sequentially, or the dose may be continuously infused, or may be a bolus injection. Further, the dosages of the therapeutic formulations contemplated within the disclosure may be proportionally increased or decreased as indicated by the exigencies of the therapeutic or prophylactic situation.

Administration of the compositions contemplated within the disclosure to a patient, preferably a mammal, more preferably a human, may be carried out using known procedures, at dosages and for periods of time effective to treat a disease and/or disorder contemplated herein in the patient. An effective amount of the therapeutic compound necessary to achieve a therapeutic effect may vary according to factors such as the state of the disease or disorder in the patient; the age, sex, and weight of the patient; and the ability of the therapeutic compound contemplated within the disclosure to treat a disease and/or disorder contemplated herein in the patient. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound contemplated within the disclosure is from about 0.01 and 10 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions contemplated within the disclosure may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds contemplated within the disclosure employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms contemplated within the disclosure are dictated by and directly dependent on (a) the unique characteristics of the therapeutic compound and the particular therapeutic effect to be achieved, and (b) the limitations inherent in the art of compounding/formulating such a therapeutic compound for the treatment of a disease and/or disorder contemplated herein.

In certain embodiments, the compositions of the disclosure are formulated using one or more pharmaceutically acceptable excipients or carriers. In certain embodiments, the pharmaceutical compositions of the disclosure comprise a therapeutically effective amount of a compound of the disclosure and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the disclosure are administered to the patient in dosages that range from one to five times per day or more. In another embodiment, the compositions of the disclosure are administered to the patient in range of dosages that include, but are not limited to, once every day, every two, days, every three days to once a week, and once every two weeks. It is readily apparent to one skilled in the art that the frequency of administration of the various combination compositions of the disclosure varies from individual to individual depending on many factors including, but not limited to, age, disease or disorder to be treated, gender, overall health, and other factors. Thus, the disclosure should not be construed to be limited to any particular dosage regime and the precise dosage and composition to be administered to any patient is determined by the attending physical taking all other factors about the patient into account.

Compounds of the disclosure for administration may be in the range of from about 1 μg to about 10,000 mg, about 20 μg to about 9,500 mg, about 40 μg to about 9,000 mg, about 75 μg to about 8,500 mg, about 150 μg to about 7,500 mg, about 200 μg to about 7,000 mg, about 3050 g to about 6,000 mg, about 500 μg to about 5,000 mg, about 750 μg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In some embodiments, the dose of a compound of the disclosure is from about 1 mg and about 2,500 mg. In some embodiments, a dose of a compound of the disclosure used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present disclosure is directed to a packaged pharmaceutical composition comprising a container holding a therapeutically effective amount of a compound of the disclosure, alone or in combination with a second pharmaceutical agent; and instructions for using the compound to treat, prevent, or reduce one or more symptoms of depressive disorder in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Although the present study discovered certain advantageous of parenteral administration of the compounds contemplated herein, the present specification is not limited thereto. Routes of administration of any of the compositions of the disclosure include oral, nasal, rectal, intravaginal, parenteral, buccal, sublingual or topical. The compounds for use in the disclosure may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present disclosure are not limited to the particular formulations and compositions that are described herein.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the disclosure may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

The present disclosure also includes a multi-layer tablet comprising a layer providing for the delayed release of one or more compounds of the disclosure, and a further layer providing for the immediate release of another medication. Using a wax/pH-sensitive polymer mix, a gastric insoluble composition may be obtained in which the active ingredient is entrapped, ensuring its delayed release.

Parenteral Administration

For parenteral administration, the compounds of the disclosure may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this disclosure include dosage forms as described in U.S. Pat. Nos. 6,340,475; 6,488,962; 6,451,808; 5,972,389; 5,582,837; and 5,007,790. Additional dosage forms of this disclosure also include dosage forms as described in U.S. Patent Applications Nos. 20030147952; 20030104062; 20030104053; 20030044466; 20030039688; and 20020051820. Additional dosage forms of this disclosure also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In certain embodiments, the formulations of the present disclosure may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the disclosure may be administered in the form of microparticles, for example, by injection or in the form of wafers or discs by implantation.

In certain embodiments of the disclosure, the compounds of the disclosure are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing

The therapeutically effective amount or dose of a compound of the present disclosure depends on the age, sex and weight of the patient, the current medical condition of the patient and the progression of the depressive disorder in the patient being treated. The skilled artisan is able to determine appropriate dosages depending on these and other factors.

A suitable dose of a compound of the present disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the modulator of the disclosure is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the patient's condition, to a level at which the improved disease is retained. In certain embodiments, patients require intermittent treatment on a long-term basis upon any recurrence of symptoms and/or infection.

The compounds for use in the method of the disclosure may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the LD50 (the dose lethal to 50% of the population) and the ED50 (the dose therapeutically effective in 50% of the population). The dose ratio between the toxic and therapeutic effects is the therapeutic index, which is expressed as the ratio between LD50 and ED50. Capsid assembly modulators exhibiting high therapeutic indices are preferred. The data obtained from cell culture assays and animal studies are optionally used in formulating a range of dosage for use in human. The dosage of such capsid assembly modulators lies preferably within a range of circulating concentrations that include the ED50 with minimal toxicity. The dosage optionally varies within this range depending upon the dosage form employed and the route of administration utilized.

Those skilled in the art recognizes, or is able to ascertain using no more than routine experimentation, numerous equivalents to the specific procedures, embodiments, claims, and examples described herein. Such equivalents were considered to be within the scope of this disclosure and covered by the claims appended hereto. For example, it should be understood, that modifications in assay and/or reaction conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

EXAMPLES

The instant specification further describes in detail by reference to the following experimental examples. These examples are provided for purposes of illustration only, and are not intended to be limiting unless so specified. Thus, the instant specification should in no way be construed as being limited to the following examples, but rather, should be construed to encompass any and all variations which become evident as a result of the teaching provided herein.

Example 1

There is considerable interest in the therapeutic potential of psychedelic drugs. Dimethyltryptamine (DMT) is a potent, rapid-onset and short-acting psychedelic drug that has not yet been independently tested for the treatment of depression. The safety, tolerability, and efficacy of intravenous DMT were investigated in treatment-resistant individuals with major depressive disorder (MDD) and healthy controls (HC) in an open-label, fixed-order, dose-escalation (0.1 mg/kg followed by 0.3 mg/kg) exploratory phase 1 study that was conducted in a typical hospital setting with strategic psychoeducation/support, but minimal psychotherapy.

Tolerability, safety, cardiovascular function, abuse liability, psychedelic and psychotomimetic effects, mood, and anxiety were assessed at each dosing session. In addition, depression was measured using the HAMD-17 in MDD participants 1 day after each dosing session. DMT was tolerated by both HC (n=3) and MDD participants (n=7) studied; there were no dropouts. HAMD-17 scores decreased significantly (p=0.017) compared to baseline in MDD participants the day after receiving 0.3 mg/kg DMT (mean difference −4.5 points, 95% CI: −7.80 to −1.20, Hedge's g=0.75). Adverse events were mostly mild. DMT increased blood pressure, heart rate, anxiety, psychedelic effects, and psychotomimetic effects, which resolved within 20-30 minutes of injection. There were no dose-related differences on measures of drug reinforcement and abuse liability. In this pilot study, intravenous DMT at doses of 0.1 and 0.3 mg/kg was mostly safe and tolerated and produced next day (rapid) antidepressant effect in patients with treatment-resistant MDD. Further rigorous trials are warranted to replicate these findings and to determine the durability of antidepressant effects.

Example 2: Related Information

There is burgeoning interest in the therapeutic potential of psychedelic compounds. Psilocybin, a prototypical serotonergic hallucinogen, has shown tantalizing therapeutic effects in several neuropsychiatric disorders.

The proliferating research with psilocybin has generated several important questions. For example, whether the promising therapeutic potential of psilocybin extends to other serotonergic hallucinogens remains unclear. Furthermore, the extent to which psychedelic effects are necessary for later therapeutic effects needs further study. Currently, psilocybin is administered orally, and thus, there is a latency to the onset of its psychedelic effects, which then last for several hours. Whether shorter psychedelic experiences suffice to elicit clinically meaningful benefit is not clear. Current models require the presence of two therapists and a specific psychotherapy protocol for the entire dosing session. The extent to which multiple therapists and integrative psychotherapy is necessary for the beneficial effects of psilocybin needs to be determined given that such a resource-intensive treatment model is challenging to implement on a wide scale and to the overwhelming majority of patients.

Like psilocybin, N,N-Dimethyltryptamine (DMT) is a serotonergic hallucinogen. DMT is present in certain plants used to make ayahuasca, a South American psychoactive brew used socially and as a ceremonial medicine by some indigenous peoples in the Amazon. Ayahuasca contains DMT and other compounds including monoamine oxidase inhibitors (MAOIs). When consumed orally, DMT is rapidly deaminated by MAOs to an inactive metabolite. However, when administered intravenously, DMT bypasses enteric metabolism and produces effects which are brief in contrast to orally administered psilocybin or ayahuasca.

The effects of DMT have been extensively studied in humans for more than 50 years. In healthy volunteers, intravenous DMT produces a range of psychedelic effects including profound dose-related alterations in perceptions, emotion, and thought. The effects include visual hallucinations, altered reality, "spiritual insights", distortion of body perception, and mood alterations or anxiety. Psychedelic effects emerge at doses higher than 0.2 mg/kg.

The effects emerge rapidly (within 2 minutes) after intravenous administration and fully resolve within about 30 minutes. At doses ranging from 0.05-0.4 mg/kg, the effects are well-tolerated in healthy controls.

The precise mechanisms underlying the psychedelic effects of DMT are not clear. DMT has agonist activity at serotonin 5-$HT_{2A}$ receptors. Other identified binding sites include various serotonin, dopamine, and adrenergic receptors, serotonin uptake transporters, trace amine-associated receptors, and sigma-1 receptors. In contrast to other psychedelics, DMT is also present at low concentrations in the brains of animals and humans at low concentrations. Because DMT activates trace amine-associated receptor 1 (TAAR1) and may be stored in vesicles at concentrations sufficient to activate receptors DMT may have a role in normal physiology and pathology. However, the extent to which interactions between exogenous DMT and endogenous DMT contribute to its overall effects is unknown.

The present inventors are unaware of any reports on the therapeutic effects of pure DMT in depression. In a small (n=6) open-label study, Osorio et al. (*Brazilian Journal of Psychiatry*. 2015; 37(1):13-20) found that a single dose of ayahuasca significantly reduced depression scores in major depressive disorder (MDD) patients without inducing mania or psychosis. More recently, Palhano-Fontes et al. (*Psychological medicine*. 2019; 49(4):655-63) reported that ayahuasca reduced depression scores in patients with treatment-resistant depression (n=29) in a parallel-arm, double-blind, randomized, placebo-controlled trial. However, while ayahuasca contains DMT, it contains numerous other potentiating constituents, including MAOIs such as harmaline that may have effects on depression independent of DMT. Furthermore, the pharmacological profile of all of ayahuasca's constituents is poorly understood (Brito-da-Costa et al., *Pharmaceuticals*. 2020; 13(11):334).

The slow onset and long duration of orally administered psilocybin and ayahuasca prompted the study on the effects of intravenous DMT, given its near instantaneous onset, yet short duration, of psychedelic effects. As the first clinical trial utilizing DMT in major depressive disorder, the present study first studied its dose-related safety, tolerability, and potential efficacy in individuals with MDD and healthy controls as a prelude to a larger trial.

Example 3: Materials and Methods

Regulatory

The present study was conducted at the Neurobiological Studies Unit (VA Connecticut Healthcare System [VACHS], West Haven, CT) with approval from the Institutional Review Boards of VACHS and Yale University School of Medicine and was monitored by an independent Data Safety Monitoring Board. The study was registered on clinical trials.gov (NCT04711915) on Jan. 15, 2021, and conducted under an approved IND (DCD #146,883).

General Study Design

The present study was an exploratory, open-label, fixed-order, dose-escalation (0.1 and 0.3 mg/kg intravenous DMT) study involving two dosing sessions at least 48 hours apart. DMT hemifumarate was synthesized at the University of Wisconsin-Madison. Participants included patients with treatment-resistant major depressive disorder (MDD) and healthy controls (HC). Participants, investigators, and raters were not masked to treatment assignment, and all participants received the study intervention.

Participants

Inclusion criteria for MDD participants: major depressive disorder (MDD) with ≥17 on HAMD-17, engaged in treatment, but treatment resistant as defined as a minimum of two prior treatment failures and confirmation of prior adequate dose and duration (Gaynes et al., *Depression and anxiety.* 2020; 37(2):134-45) and at least one failed antidepressant trial in the current depressive episode. MDD participants exclusions: the presence of a psychotic disorder, unstable medical co-morbidities, history of mania, and recent high risk for suicide or homicide. Exclusion criteria common to HC and MDD groups: pregnancy, current or recent drug dependence, lifetime history of hallucinogen use disorder, regular use of psychedelics, and current use of over-the-counter products with serotoninergic properties.

Recruitment

The HC group was recruited from the community using advertisements, online postings, and word of mouth. MDD participants were recruited from the community using clinician referrals, advertisements, online postings, and word of mouth.

Screening

Eligible participants completed a thorough psychiatric and medical history and examination including comprehensive laboratory testing. For MDD participants, collateral and support from the participant's primary mental health clinician was required.

Preparation

If eligible, participants met with the study psychiatrists for a preparatory session of about 45 minutes, during which participants were provided information about DMT's psychological effects, and approaches to navigate the experience itself. Furthermore, MDD participants were invited to discuss their mood symptoms and their depression history. Participants were told that they would receive a 0.1 mg/kg followed by a 0.3 mg/kg dose of DMT. Furthermore, they were told that while they may not benefit from study participation, their participation may lead to knowledge that may help others.

Drugs

Since free base DMT is not water soluble, water-soluble N,N-dimethyltryptamine hemifumarate was prepared that was minimally 99.9% pure for intravenous injection. Detailed synthetic and analytic procedures have been previously published. (Cozzi et al., *Drug Test Anal.* 2020:1-11) DMT hemifumarate was compounded into a sterile investigational product (20 mg/mL injection, 1 mL vial). Only if participants tolerated the first dosing (0.1 mg/kg DMT) session, were willing to continue, and the research team approved, was the next dose (0.3 mg/kg DMT) session scheduled.

Test Sessions

On arrival, participants were first checked for recent alcohol and drug use and completed pre-dose/baseline assessments (FIG. 6). Participants were dosed in a booth containing a medical-grade reclining chair and desk that was lit with overhead fluorescent lighting. There was no art adorning the room and no music was played. Participants were provided pillows and hospital-issued linens. The two psychiatrists stood on either side of the medical chair, with a research nurse and research assistants immediately behind the subject. After connecting the DMT-containing syringe to the intravenous port, the impending administration of DMT was announced. Participants were administered DMT by intravenous push over 30-60 seconds.

Blood pressure was measured at baseline and 5, 10, 15, 20, 30, 45, 60, and 120 minutes after drug administration. Heart rate and pulse oximetry were measured continuously. Subjective drug effects were measured 60 min before, as well as 30 and 120 min after drug administration.

Given the intensity and brevity of DMT effects, participants were allowed a mostly uninterrupted experience with psychiatrists utilizing a non-directive and supportive approach. Participants were asked how they were feeling at the same time points as the physiological recordings; no psychotherapy was provided. Rescue medications for psychological distress (lorazepam and risperidone) and hypertension (labetalol) were available. Prior to discharge, a field sobriety test and mini-mental status examination were conducted to confirm return to baseline.

Debriefing

For the approximately 2 hours between the waning of DMT and the time of discharge, participants were debriefed by a psychiatrist (SAS). The day after each session, participants were contacted via telephone to check on their well-being, to monitor for any adverse events, and, in MDD participants, to administer the HAMD-17.

Outcomes

Tolerability defined by the US FDA as "the degree to which overt adverse effects can be tolerated" by a subject was assessed. At the end of the test day, after all drug effects had worn off, participants were asked to score 1) the overall experience on a visual analog scale [VAS] (0=intolerable to 100=well-tolerated), 2) the likelihood of using the drug again (0=not at all to 100=most of all), and 3) how much they were willing to pay for the experience ($0 to $100). Similarly, all participants were asked to rate anxiety on a VAS (0=not more than usually to 100=much more than usual); MDD participants also rated depression. Safety defined by the US FDA as "the risk to the subject or patient from a drug or biologic assessed by tests" was assessed by monitoring vital signs and recording adverse events. (Shader, *Clinical Therapeutics.* 2018; 40(5):672-73). The quality and intensity of psychedelic effects were captured using a 23-item Psychedelic Effects Visual Analog Scale. (Timmermann et al., *Scientific reports.* 2019; 9(1):1-13) To capture the effects of DMT on perception, thought, and sensory processing, participants were administered the Psychotomimetic States Inventory. (Mason et al., *Schizophrenia research.* 2008; 103(1-3):138-42) Shortly after resolution of effects, participants were instructed to retroactively rate the effects experienced during the peak effects. Depression was measured using the clinician administered HAMD-17 at baseline (at screening) and one day after each dosing session. The HAMD-17 was chosen as the primary efficacy measure due to its high reliability and validity. (Williams, et al., *International clinical psychopharmacology.* 2008; 23(3): 120-29). The day after each dose session was chosen as the primary efficacy point because the acute psychedelic effects to obscure any meaningful changes in mood were unwanted.

Statistical Analysis

This exploratory-feasibility study was conducted to investigate the tolerability, safety, and potential efficacy of two doses of DMT to inform and power a larger, double-blind, randomized, placebo-controlled, crossover study. For subjective measures including the psychedelic effects VAS, PSI, and VAS (anxiety and depression), peak change from baseline was calculated and analyzed using paired t-test, when data met parametric assumptions, or nonparametrically, using two-tailed Wilcoxon signed-rank tests. Cardiovascular parameters were analyzed using repeated measures ANOVA with dose as a between subject factor and time as the within subject factor. HAMD-17 scores for each dose were compared to baseline using paired t-tests. Mean differences are presented with 95% confidence intervals and effect size is reported using Hedge's g formula. Multiple comparison correction was performed for PSI subscales (Bonferroni) and VAS psychedelic effect items (FDR), associated with reduced power, in order to minimize type I errors (Benjamini et al., *The Lancet Psychiatry.* 2016; 3(7):619-27).

Example 3: Selected Results

Figure 18:
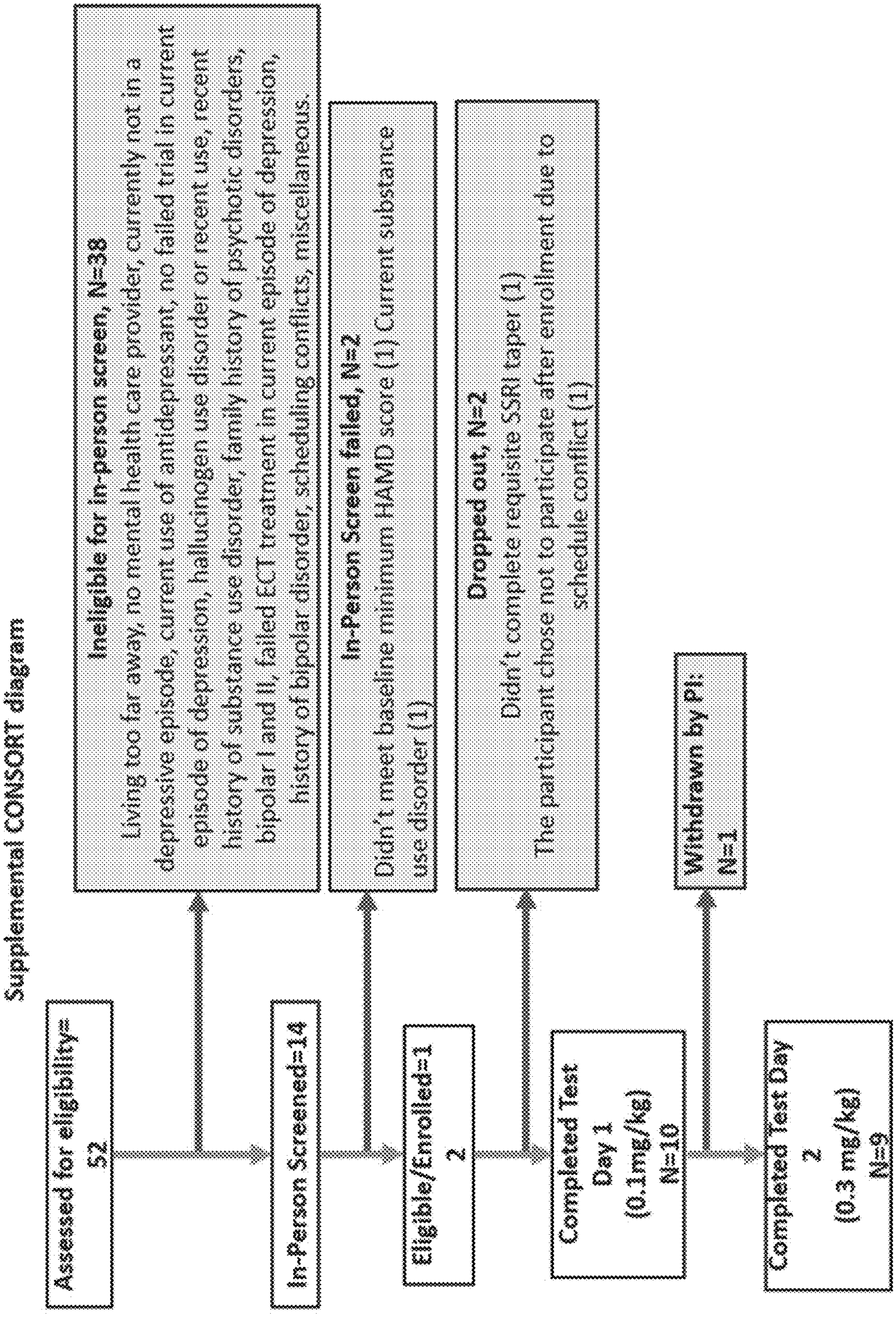
FIG. 18 depicts a supplemental CONSORT diagram, in accordance with some embodiments.

Enrollment occurred between Mar. 17 and Oct. 12, 2021. From the 52 individuals who were initially considered for the study and for a telephone screen (See the Supplemental CONSORT diagram of FIG. 18), 14 were selected for an in-person screening visit, and 12 (3 HC and 9 with current MDD) were enrolled in the trial. 2 MDD participants dropped out before randomization. Amongst the 7 MDD participants who received DMT, 4 were self-referred and 3 were clinician-referred. Participants' demographic and clinical characteristics are shown in FIGS. 1A-1B. Three of 7 MDD participants met criteria for severe depression at baseline (HAMD-17 score ≥24) while the remaining four met criteria for moderate severity depression (HAMD-17 score 17 to <24). As a prerequisite to participation, all MDD participants were engaged in treatment and were not taking any antidepressant medication that could interfere with DMT effects. Except for one participant (one month), all the others had last taken antidepressants more than three months before their first test day. Only one MDD participant withdrew taking antidepressants in order to participate. A total of 10 subjects were studied prior to the batch of DMT expiring.

Tolerability

Figure 7:
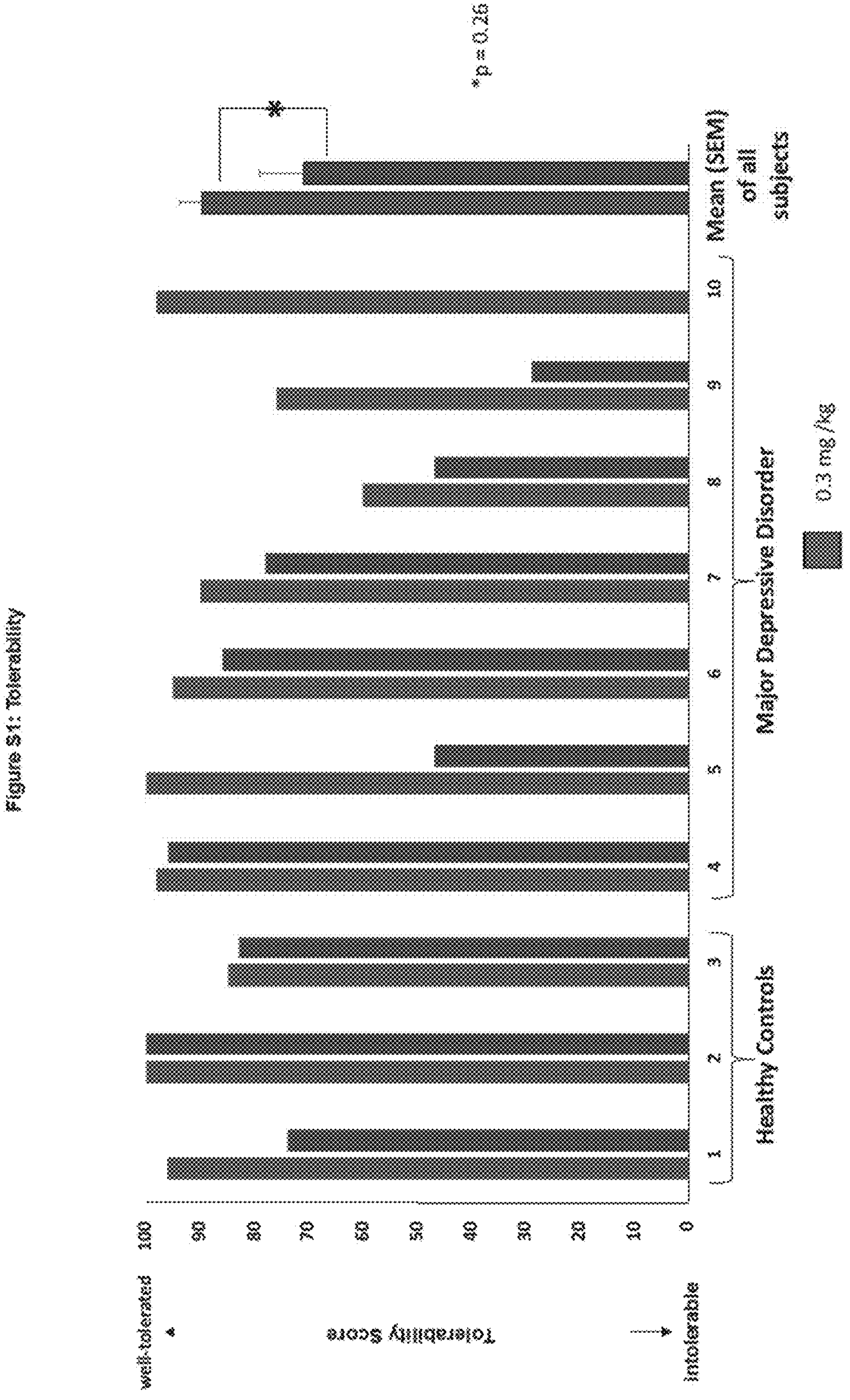
FIG. 7 depicts the tolerability, in accordance with some embodiments. Specifically.

Participants reported overall tolerability (0=intolerable to 100=well-tolerated) as 89.80 (SD 12.95) for the 0.1 mg/kg dose session and 71.11 (SD 24.52) for the 0.3 mg/kg dose session (difference −17.78 [95% CI −32.81 to −2.75] t=−2.72, p=0.026) (FIG. 7).

After completion of the 0.1 mg/kg dose session, all participants reported willingness to return for the second dose session (0.3 mg/kg). Furthermore, on completion of the first dose session (0.1 mg/kg), the study psychiatrists determined that all the participants who completed the first dosing session were appropriate for continuation to the second dose day based on a review of the self-reported effects, study-clinician observed effects, cardiovascular parameters, participants debriefing, and clearance testing.

Safety

Figure 2B:
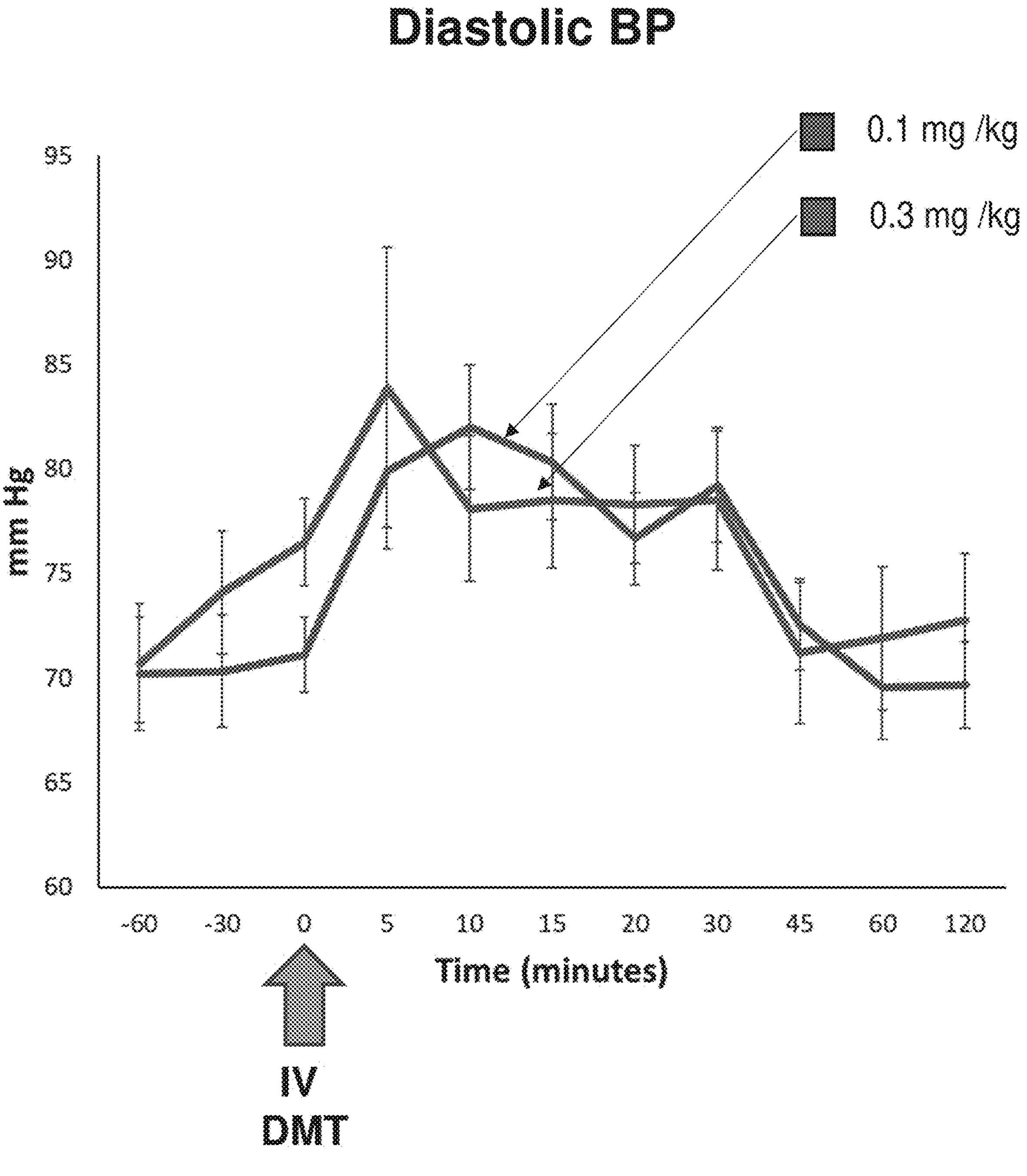
Figure 2C:
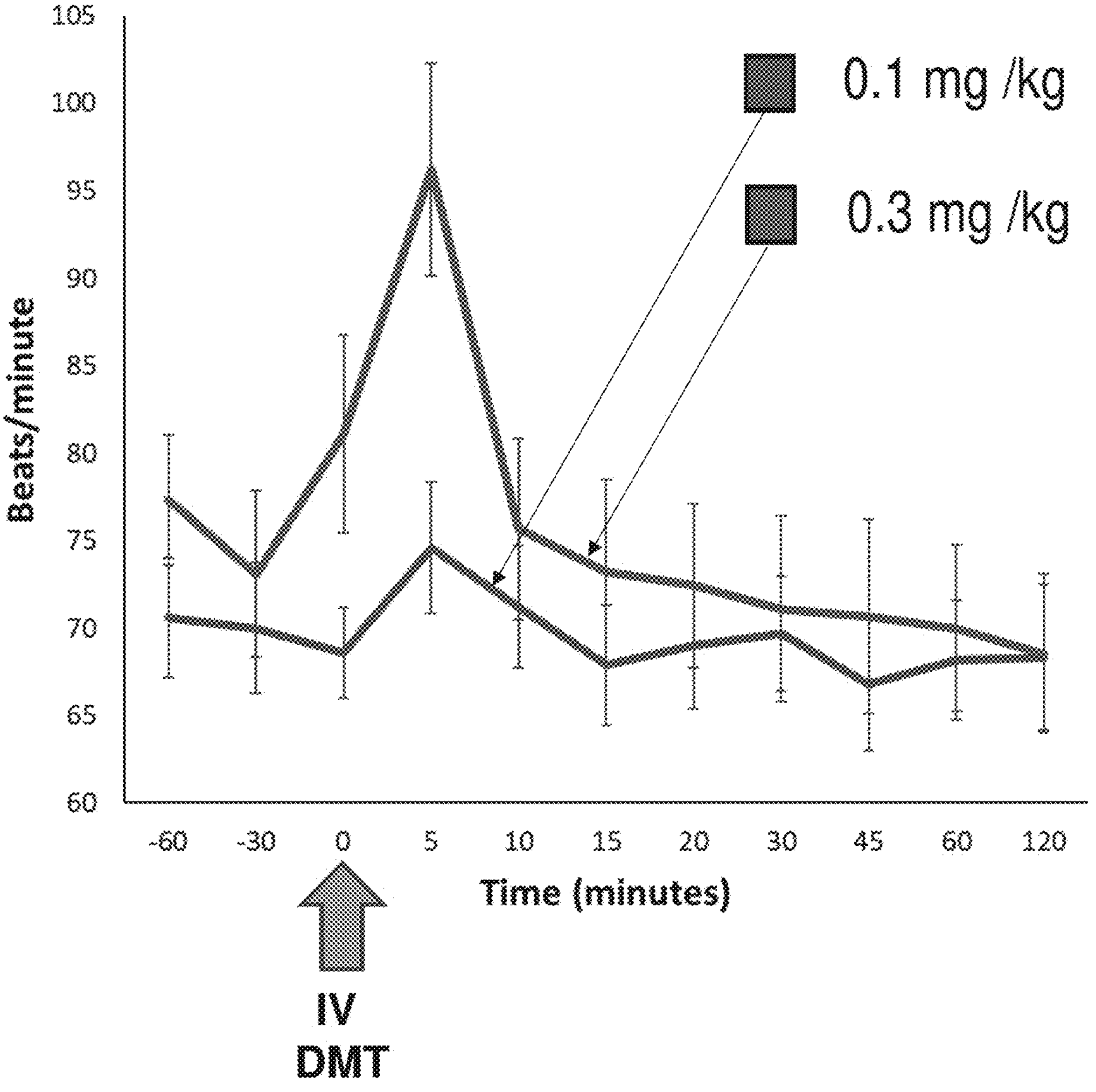

DMT increased systolic and diastolic blood pressure, and heart rate (FIGS. 2A-2C); while there was a significant time effect for both doses, there were no significant dose or dose-time effects.

Post-hoc analyses revealed statistically significant increases in systolic pressure at the +5, +10, and +15 minute time points relative to baseline; significant increases in diastolic pressure at +5, +10, +15, +20, and +30 minutes relative to baseline; and significant increases in heart rate at the +5 minute time point relative to baseline (FIG. 9).

Adverse Events

The most common adverse events (AEs) were transient anxiety prior to administration and drug onset (n=6), transient headache (n=2) during onset and after resolution of drug effects, and transient hypertension (n=2) before dose and during onset of effects (FIGS. 3A-3B). Some of the AEs were deemed definitely related to DMT effects while others were deemed unrelated. There was one serious adverse event in a female participant who had significant asymptomatic bradycardia and hypotension that was addressed by placing the participant in Trendelenburg position and increasing intravenous saline (FIG. 17). None of the participants experienced any clinically relevant psychotic symptoms. All participants passed a standard field sobriety test and predose baseline-matched Mini-Mental Status Exam prior to discharge. No rescue medications were used during any dosing session to address psychological or physiologic adverse events reported.

Subjective Effects

Figure 11:
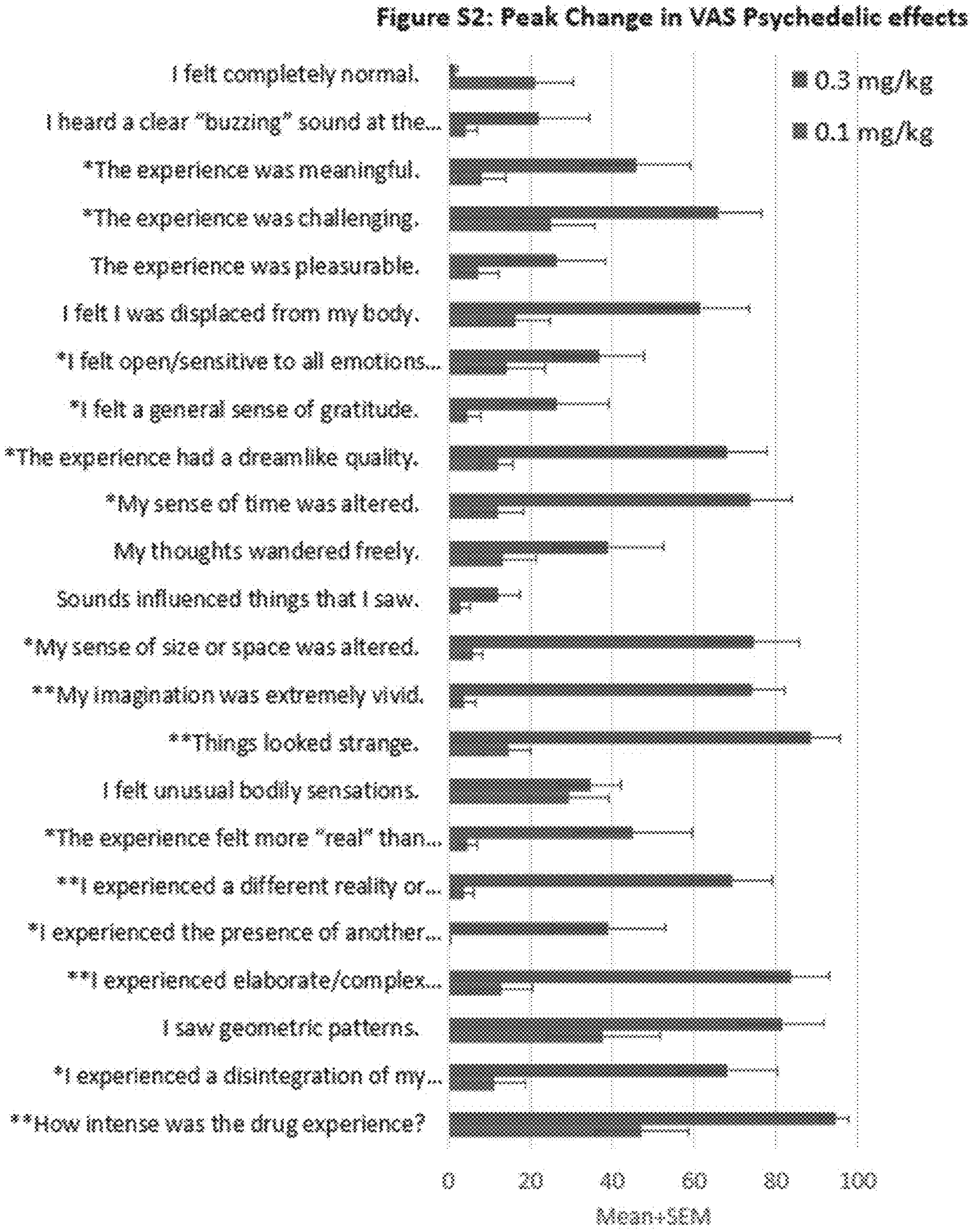
FIG. 11 depicts the peak change in VAS psychedelic effects, in accordance with some embodiments. Specifically, the figure depicts peak change in VAS psychedelic effects at 0.1 mg/kg and 0.3 mg/kg dosages. Error bars indicate standard errors of the mean (S.E.M.).

DMT's acute psychedelic effects typically became detectable between 2 and 5 minutes of administration, peaked between 5-10 minutes after dosing, and completely subsided by 30 minutes. While there were no significant scores on any of the 23-item VAS psychedelic effects at baseline, scores increased with both doses at the +30 minute rating. Peak change in VAS psychedelic composite score was 13.16 (SD 11.91) for the 0.1 mg/kg session and 55.83 (SD 23.89) for the 0.3 mg/kg dose (difference 42.67 [95% CI 33.30 to 52.03]; z=4.11; p<0.0001; Hedge's g=2.2) (FIG. 4). There were significant dose-related differences on 16 of the 23-items (FDR correction, q=0.05) (FIG. 10). The top five ranked items with significant dose-related differences (p, adjusted ≤0.01) were 'intensity of experience' (p=0.002), 'complex visual images' (p=0.004), 'experienced different reality/dimension' (p=0.006), 'things looked strange' (p=0.008), and 'imagination was very vivid' (p=0.01) (FIGS. 10-11).

Figure 12:
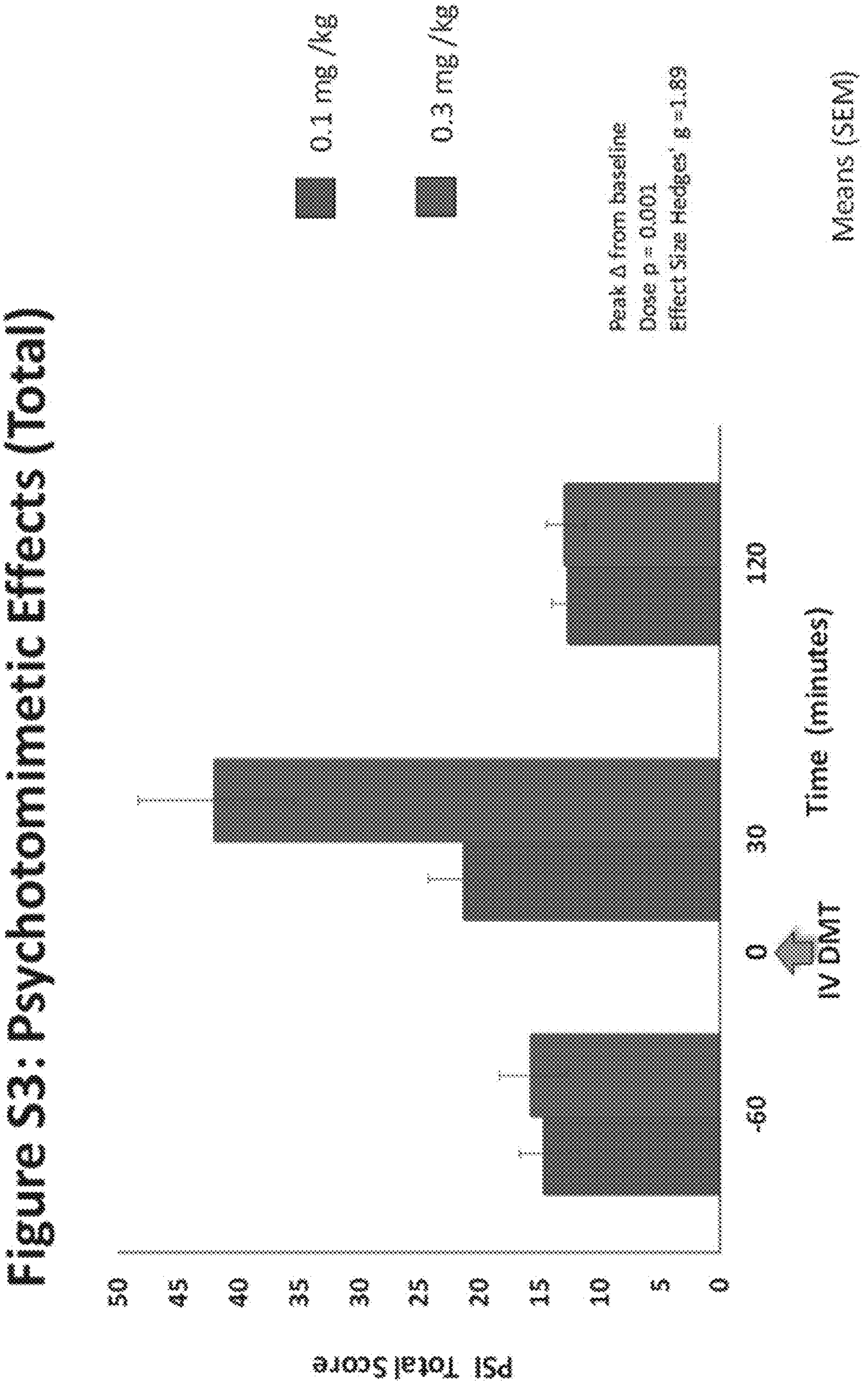
FIG. 12 depicts the psychotomimetic effects, in accordance with some embodiments. The figure depicts the total score, which is a sum of the scores of the six factors. Acute effects measured via the Psychotomimetic States Inventory (PSI). Values are the mean scores of the peak changes plus the positive standard errors of the mean (S.E.M.) for each time point (−60:60 minutes before IV DMT administration, +30, +120: 60 and 120 minutes after IV DMT).
Figure 14A:
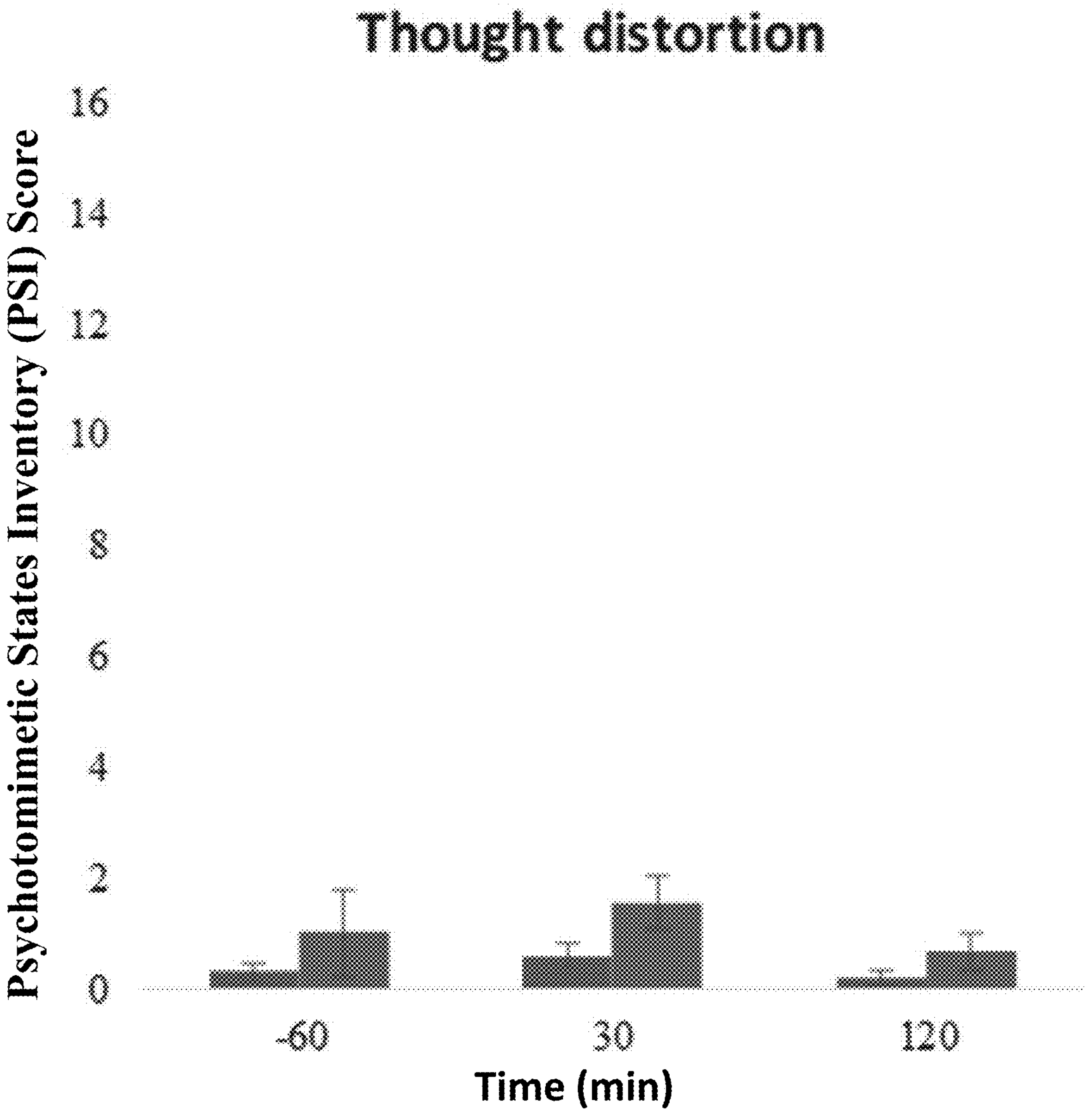
FIGS. 14A-14F depict the psychotomimetic effects in subscales, in accordance with some embodiments. Acute effects are measured via the Psychotomimetic States Inventory (PSI). Values are the mean scores of the peak changes, plus the positive standard errors of the mean (S.E.M.) for each of the six factors of the PSI, for each time point (−60:60 minutes before IV DMT administration, +30, +120: 60 and 120 minutes after IV DMT).
Figure 14B:
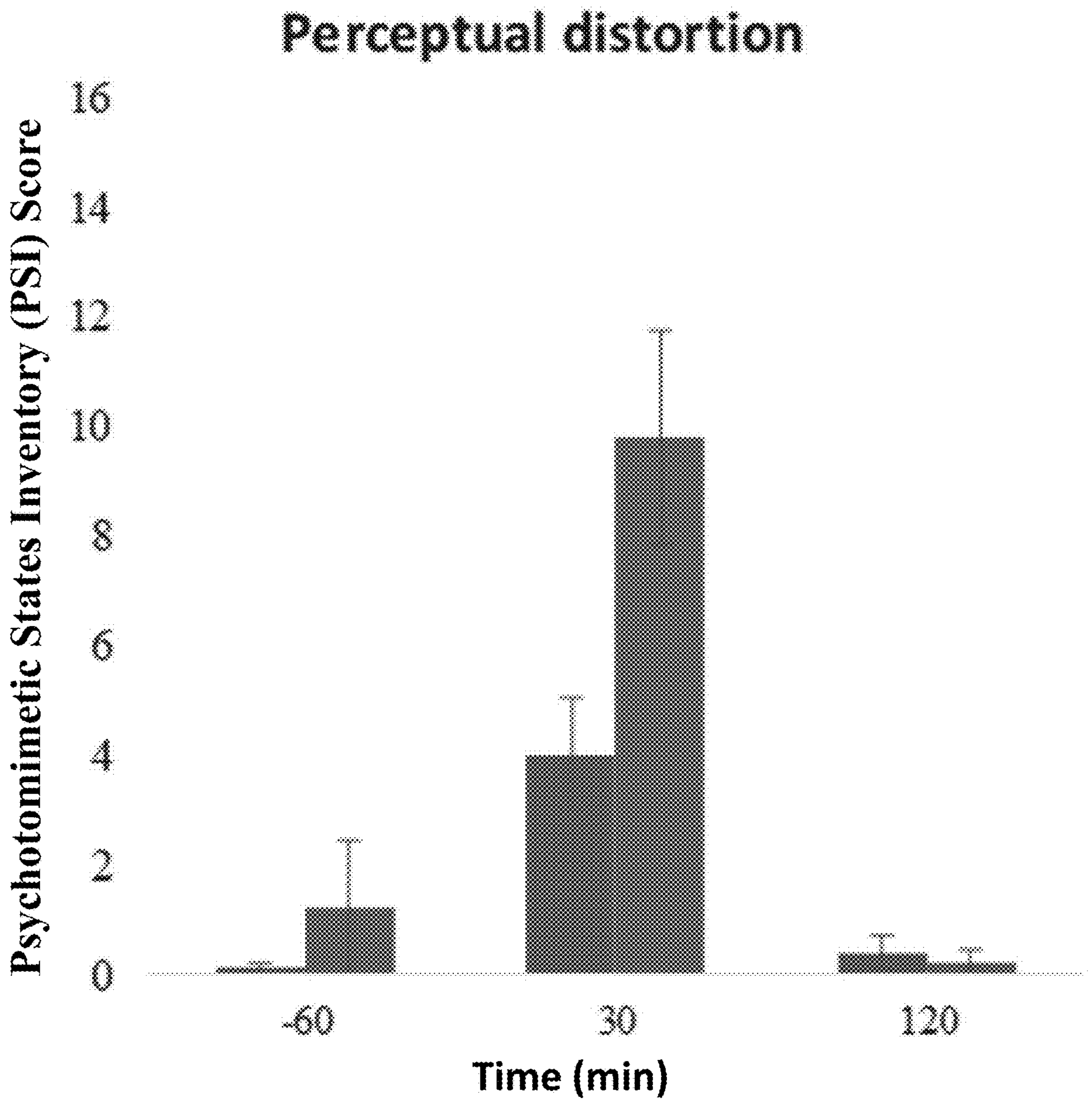
Figure 14C:
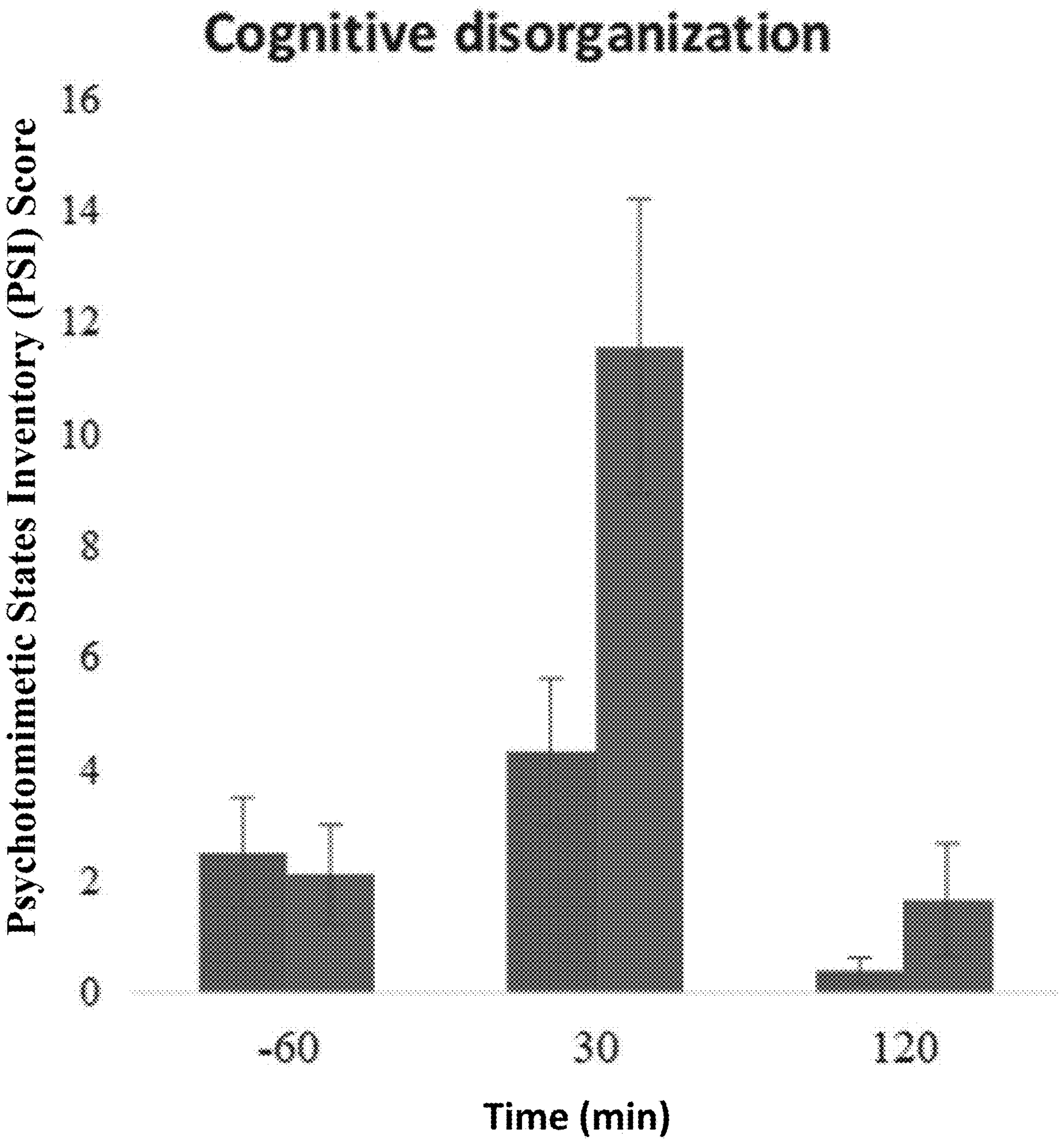
Figure 14D:
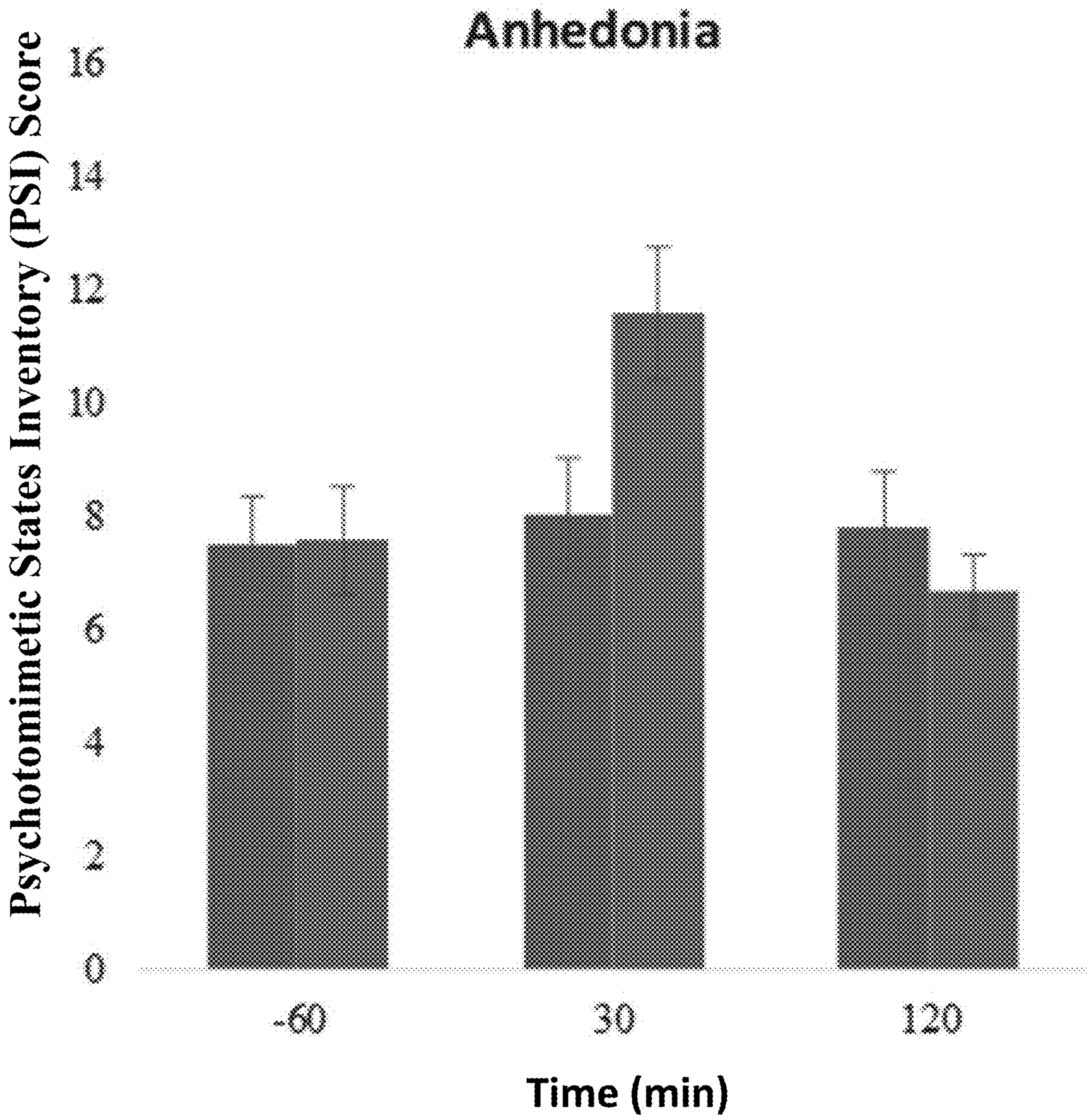
Figure 14E:
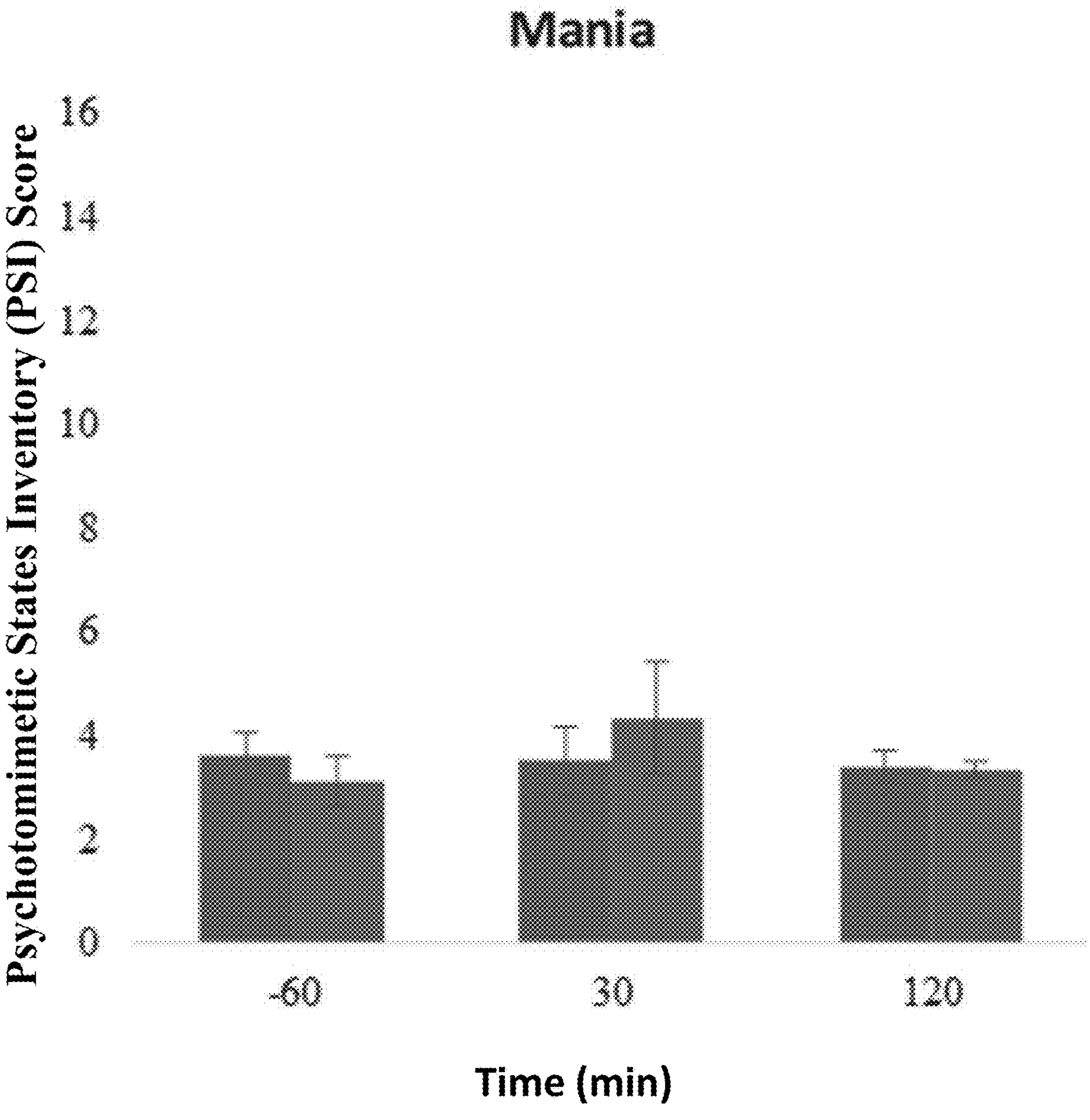
Figure 14F:
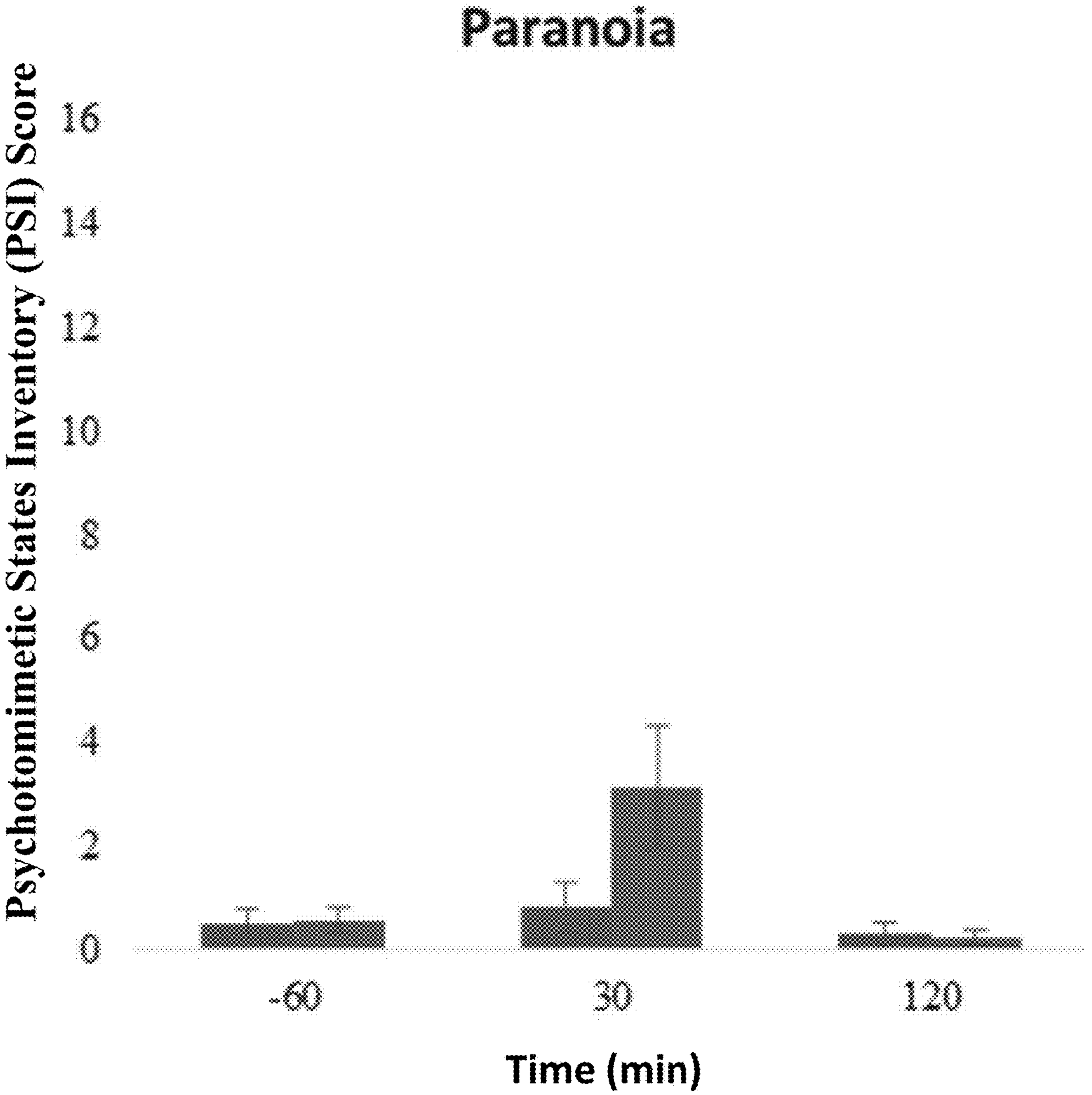

Mean peak change in Psychotomimetic States Inventory (PSI) scale total score was 7.33 (SD 7.62) for the 0.1 mg/kg session and 31.67 (16.57) for the 0.3 mg/kg session (difference 24.33; 95% CI 12.74 to 35.94: t=4.84: p=0.001; Hedge's g=1.89) (FIGS. 4 and 12). The dose-related difference on peak change in PSI subscales was significant only for the perceptual disturbance subscale (p<0.005) (FIG. 13).

Figure 15:
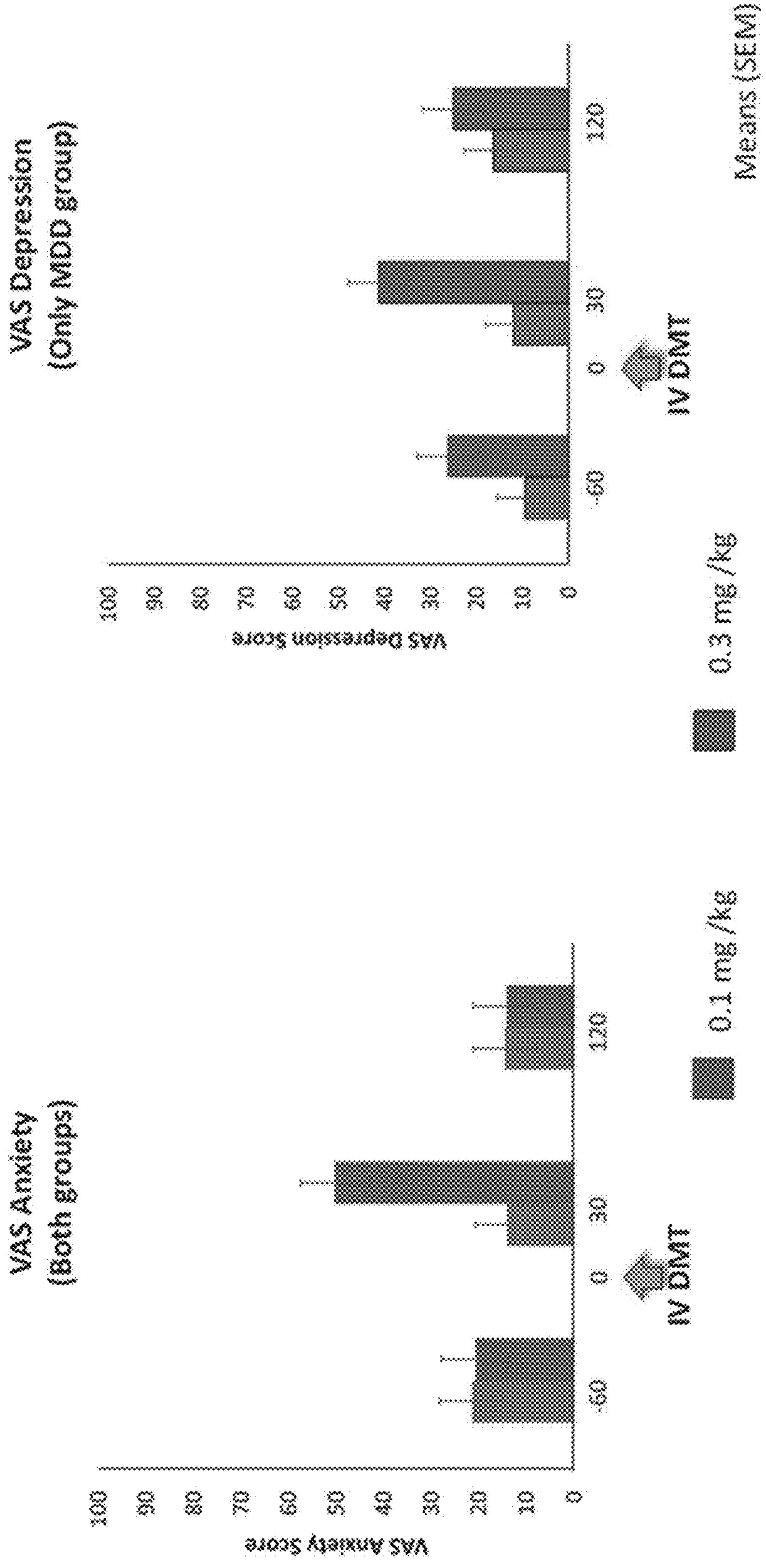
FIG. 15 depicts in Session VAS anxiety and depression, in accordance with some embodiments. Values are mean scores of the peak changes in VAS Anxiety and Depression, at 0.1 mg/kg and 0.3 mg/kg dosages. Error bars indicate standard errors of the mean (S.E.M.) for each time point (−60:60 minutes before IV DMT admiration, +30, +120: 60 and 120 minutes after IV DMT).

Peak change in VAS anxiety scale administered to all participants was 2.56 (SD 31.8) on the 0.1 mg/kg session and 29.67 (SD 39.96) on the 0.3 mg/kg session; (difference 27.11 [95% CI −14.30 to 68.53] z=1.1, p=0.26). Peak change in VAS depression administered only to MDD participants was 6.83 (SD 28.94) for the 0.1 mg/kg session and 14.83 (SD 37.79) on the 0.3 mg/kg session (difference 8.00 [95% CI −41.47 to 57.47] z=0.11, p=0.92 (FIGS. 4 and 15).

On measures of drug desirability, participants reported overall willingness to use DMT as 24.00 (SD 17.91) for the 0.1 mg/kg session and 22.44 (SD 22.72) for the 0.3 mg/kg session; (difference −1.56 [95% CI: −16.74 to 13.62] z=−0.14, p=0.90). Participants monetized the value of drug effects (scale from 0-100 dollars) as 25.56 (SD 29.07) for the 0.1 mg/kg session and 24.78 (SD 33.36) for the 0.3 mg/kg session; (difference −0.78 [95% CI −32.38 to 33.94] z=−0.14, p=0.89) (FIG. 16).

Next Day Depression Ratings

Figure 5:
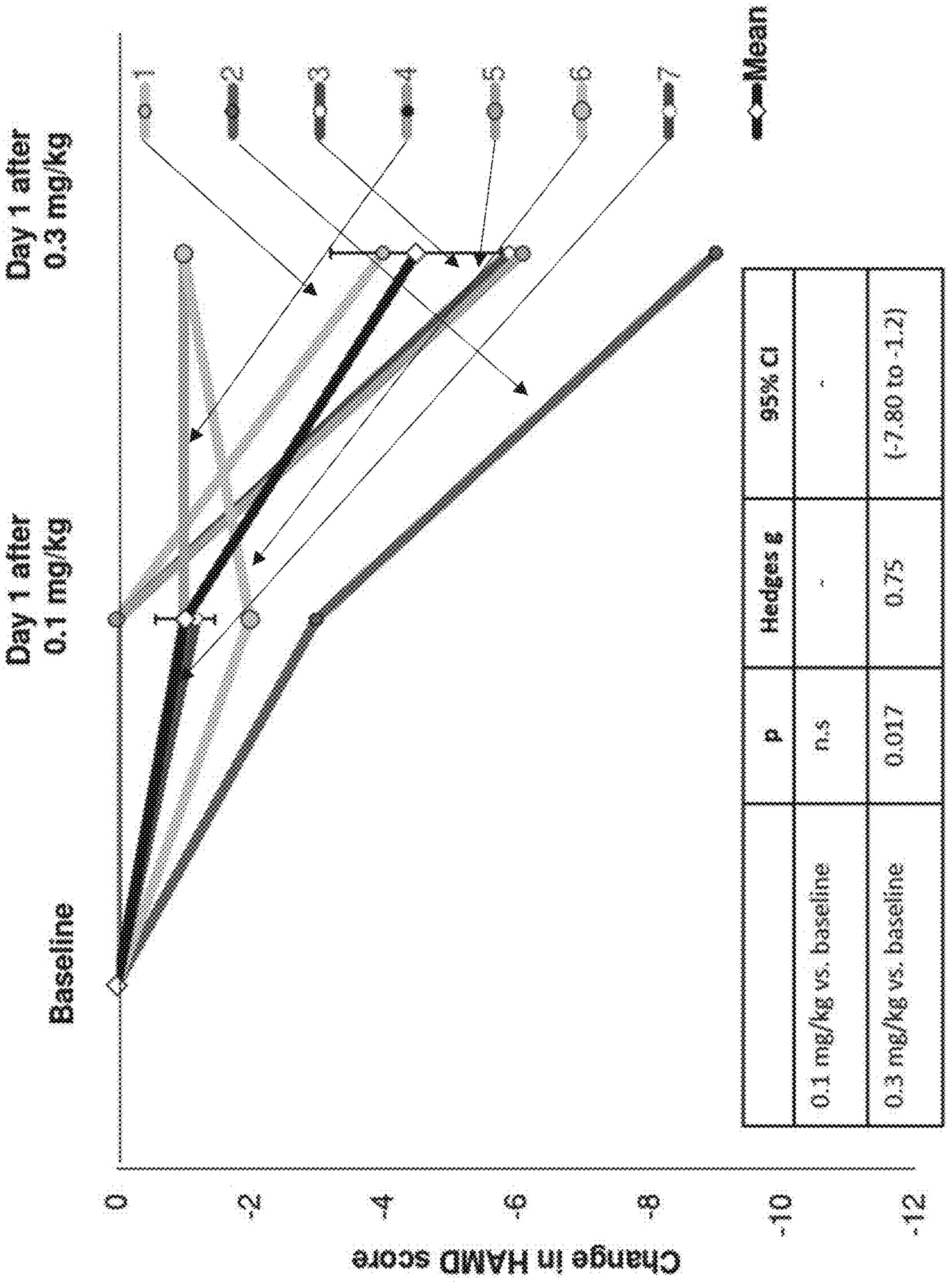
FIG. 5 depicts the change in depression in the participants, in accordance with some embodiments.

Most MDD participants showed a nominal reduction in depression severity on the HAMD-17 after the 0.1 mg/kg session (FIGS. 5 and 17). HAMD-17 depression scores were significantly reduced from baseline (23.86 (SD 4.45)) to post-0.3 mg/kg session (20.20 (SD 7.82)); (difference −4.5 [95% CI: −7.80 to −1.20] t=−3.50, p=0.017; Hedge's g=0.75). Difference in HAMD-17 was also significant between the 0.1 mg/kg session and 0.3 mg/kg session; (difference −3.5 [95% CI: −6.87 to −0.013] t=−2.67, p=0.044). One treatment-resistant MDD participant who experienced a significant improvement in depression, requested additional dosing.

Example 4

To the knowledge of the inventors, this is the first report of the safety, tolerability, and efficacy of DMT in MDD. Intravenous DMT can be safely administered to and tolerated by individuals with moderate to severe, treatment-resistant MDD, and it may have next day antidepressant properties.

The most novel finding of this study was the significant reduction in HAMD-17 scores one day after receiving DMT 0.3 mg/kg in MDD patients who had failed several previous antidepressants trials and who had been chronically ill (average duration of illness was 27 years). The mean reduction in HAMD-17 score was about 4.5 points the day after receiving 0.3 mg/kg, a medium to large effect size (Hedges g=0.75). Of note, HAMD-17 scores changed nominally the day after the 0.1 mg/kg dose, and the difference between the two doses was significant. However, because of the fixed order and the lack of any measure of depression immediately prior to the 0.3 mg kg DMT session, it is not possible to determine the extent to which carryover effects from the 0.1 mg kg DMT session. Consistent with the known heterogeneity of MDD, some participants had greater reductions in HAMD-17 scores than others. One MDD participant had a profound and sustained improvement in depression (corroborated by her partner) and requested receiving additional doses.

The magnitude of antidepressant effects with DMT were smaller than those reported by Carhart-Harris et al. with psilocybin (*The Lancet Psychiatry.* 2016; 3(7):619-27). A number of differences between the two studies including the samples studied, the setting, augmentation with psychotherapy, the duration of psychedelic effects, the timing of assessments and the route of administration of the drugs, may have accounted for the differences in the magnitude of effects. A direct comparison of the two drugs head on will be necessary to determine their differences and similarities.

Considerable importance has been given to the centrality of set and setting in psychedelic treatment models. Recent psychedelic studies are typically conducted settings that are adorned with art, plants, flowers, and homey furnishings, painted in warm colors, and lit with muted lighting. Studies often include specific music. Furthermore, psychotherapy is considered a fundamental part of the current psychedelic treatment paradigm. In contrast, this DMT study was conducted in a typical hospital setting, and participants received strategic education and psychological support but minimal psychotherapy, similar to ketamine. Despite the hospital setting and minimal psychotherapy provided in this study, depression scores decreased with DMT. Neither psychedelic/psychotomimetic effects (ASC/PSI) significantly correlated with change in depression score from baseline to post-0.3 mg/kg dose.

The present study provides information on the safety and tolerability of DMT in depressed individuals. DMT produced transient dose-related increases in perceptual alterations (FIGS. 11-13 and 14A-14F). The largest changes were on items of intensity, visual imagery, and alternate reality experience. Participants reported transient increases in anxiety. There were no serious psychiatric adverse events. Consistent with the literature, DMT produced transient increases in blood pressure and heart rate. However, there was one serious adverse event (SAE) of one participant who had precipitous hypotension and bradycardia lasting 5 minutes after receiving 0.3 mg/kg DMT; there were no sequelae. Given that DMT typically increases blood pressure, the serious adverse event (SAE) was determined to be an interaction between the participants' (undisclosed) history of autonomic instability and DMT effects. The cardiovascular effects of DMT warrant careful screening for cardiovascular risk factors, and for implementing procedures in place to manage cardiovascular events. Participants reported that the experience was intense and challenging (ASC scale items), and transient increase in anxiety. Yet participants reported that the experience was pleasurable and meaningful (modified ASC scale items), and that they were willing to return to receive IV DMT 0.3 mg/kg. Participants rated the tolerability of the 0.1 and 0.3 mg/kg doses as 89.80 (SD 12.95) and 71.11 (SD 24.52), respectively. Furthermore, no participants dropped out from the present study. Collectively taken while intense and challenging, IV DMT was mostly safe and tolerated. Larger studies may be necessary to more fully evaluate the safety and tolerability of IV DMT.

That immediately after the dosing session, participants were willing to pay only $25 for the experience ($0-100), and reported being less likely to use DMT, suggests that intravenous DMT has low abuse potential.

The strengths of the study include the use of a sub-psychedelic and psychedelic dose, the inclusion of both healthy control and MDD participants, and the study of treatment-resistant MDD.

In conclusion, the findings of this exploratory study provide support for DMT's tolerability, safety, and potential rapid antidepressant effect. In contrast to other psychedelic treatment models, reductions in depression were observed the day after DMT dosing, and occurred within a typical hospital setting, and without intensive psychotherapy. This intriguing finding suggests it may be easier to implement DMT for the treatment of MDD.

Example 5: Additional Information

Detailed Inclusion Exclusion Criteria

Inclusions Criteria for Depressed Subjects:

1) Diagnostic and Statistical Manual (DSM) 5 major depressive disorder 2) moderate to severe degree (17+ on the 21-item Hamilton Depression Rating scale [HAM-D]), 3) an unsatisfactory response to at least one adequate antidepressant trial (at least 6 weeks on a therapeutic dose) during the current depressive episode, 4) engaged in treatment for depression and willing to continue treatment for the duration of the study.

Exclusion Criteria for Depressed Subjects were:

1) current or previously diagnosed psychotic disorder, 2) medically significant condition rendering unsuitability for the study, 3) clinically significant risk for suicidal or homicidal behavior during course of the study, 4) history of mania, 5) current antidepressant treatment (which might interfere [blunt] DMT effects).

Inclusion Criteria for Healthy Controls:

1) no current DSM-5 psychiatric disorder, excluding nicotine and caffeine use disorder, 2) no lifetime use of psychiatric medication >3 months (proxy for psychiatric disorders).

Exclusion Criteria Common to Both Groups Included:

1) positive pregnancy test at screening or during the study, 2) recent (within 3 months) or current drug or alcohol dependence, 3) lifetime history of hallucinogen use disorder, 4) regular use of serotoninergic hallucinogens (i.e., DMT and psilocybin related compounds), 5) medical condition deemed by the PI to be unstable, 6) currently taking of over the counter products such as 5-hydroxytryptophan and St. John's wort.

Screening Process

Preliminary eligibility was determined by phone, and if eligible, subjects were invited for a more in-depth in-person evaluation. After obtaining written informed consent, the following was conducted: a thorough evaluation of the patient's physical and mental health, a psychiatric interview (SCID-5-CT), 21-item HAM-D, the Schizotypal Personality Questionnaire, and the Patient Health Questionnaire 9. For MDD subjects, the individual's mental health clinician was contacted to confirm the diagnosis, treatment, and mental health history. In order to participate, MDD subjects needed to have their mental health clinician support their participation in the study. Vital signs, weight, and electrocardiogram were recorded, and a physical examination was conducted. Laboratory tests including urine toxicology for street drugs, urinalysis, serum chemistry, hematology, and liver function were conducted. During preparatory session, MDD subjects were invited to discuss their mood symptoms and their history relevant to depression, e.g., trauma, interpersonal challenges, etc.

Detailed Description of Dosing Session

Subjects attended two dosing sessions that were separated by at least 72 hours. On the first test session, subjects received a single dose of 0.1 mg/kg and if they tolerated the dose, were willing to continue, and further participation was approved by the research team, a second session was scheduled during which the subject received a single dose of 0.3/mg/kg. No more than one subject was dosed on any given testing day. Subjects arrived at the research facility (Neurobiological Studies Unit at the Veterans Affairs Hospital, West Haven, CT) at 0800 h, gave a urine sample for toxicology testing, submitted to a breathalyzer test for alcohol use, and completed pre-dose/baseline assessments described below (FIG. 6). In advance of dosing session, subjects were directed to obtain alternative transportation on test days and advised against operating machinery or an automobile. After confirming absence of alcohol intoxication by breathalyzer, recent street drug exposure by urine toxicology (cocaine, benzodiazepines, opiates, cannabinoids, stimulants), compliance with study prohibitions, and measurement of vital signs, an intravenous line with normal saline was inserted by a research nurse. Subjects were then taken to the dosing room, which markedly differs from the setting that other psychedelic studies are being conducted. The dosing room was 8×6×8 ft in size, contained a hospital issued reclining chair, and a desk with a monitor (not utilized). There was no art adorning in the room and no music was played. Lighting was from an overhead fluorescent light. Subjects were provided pillows and hospital issued white blankets and sheets. Subjects were transitioned into the dosing room and seated on a reclining hospital chair. Discharge clearance entailed field sobriety testing as well as mini-mental status examination to confirm return to baseline.

Detailed Description of Outcome Measures

Tolerability and Drug Reinforcement Measures: Subjects were asked at the end of the test day after all drug effects had worn off, to score 1) the overall experience on a visual analog scale [VAS] (0=intolerable to 100: well-tolerated), 2) the likelihood of using the drug again (0=not at all to 100=most of all), 3) how much they were willing to pay for the experience ($0 to $100).

Psychedelic Effects: The quality and intensity of psychedelic effects were captured using a 23-item Visual Analog Scale derived from the longer Aletered States of Consciousness scale as reported by Timmerman et al. (*Sci Rep.* 2019 Nov. 19; 9(1):16324). The scale has been shown to be sensitive to the effects of DMT compared to placebo.

Psychotomimetic Effects: To capture the effects of DMT on perception, thought, and sensory processing, subjects were administered the Psychotomimetic States Inventory (Mason et al., *Schizophr Res.* 2008 August; 103(1-3):138-42) which has subscales for delusory thinking, perceptual distortion, cognitive disorganization, anhedonia, mania and paranoia.

Both the VAS Psychedelic effects, and PSI were measured before dose administration, shortly after resolution of effects, and again near time of discharge. Subjects were instructed to retroactively rate the effects during the peak effects, given that they might not be able to accurately assess and report effects while immersed in the peak effects. Similarly, subjects were asked to rate on a VAS scale (0=not more than usually to 100=much more than usual) anxiety and depression (only MDD subjects). In addition to day-after dosing follow up, subjects were contacted 1, 2, and 12 weeks after completion of the last dosing session to follow up on safety and wellbeing.

Statistical Plan

This exploratory-feasibility study was conducted to inform the tolerability, safety, and potential efficacy to inform, in order to power a larger, double-blind, randomized, placebo-controlled, crossover study. For subjective measures including the psychedelic effects VAS, PSI, and VAS (anxiety and depression) peak change from baseline was calculated and analyzed using paired t-test, when data met parametric assumptions, or nonparametrically, using two-tailed Wilcoxon signed-rank tests. VAS measures of tolerability, willingness to pay for the experience, and likelihood to use DMT were analyzed similarly. Vital signs which were measured repeatedly on each test day were confirmed for normality and absence the presence of outliers and analyzed using GLM repeated measures ANOVA with dose as a between subjects' factor and time as the within subject's factor. HAM-D for each dose was compared to baseline using paired t-tests. Mean differences were presented with 95% confidence intervals and effect size was reported using Hedge's g formula. For 23-item VAS psychedelic effects, multiple comparison correction was performed using false discovery rate (FDR) correction for all measures in order to increase statistical power and minimize type II errors (Benjamini and Hochberg, Journal of the Royal Statistical Society. Series B (Methodological) Vol. 57, No. 1 (1995), pp. 289-300). For PSI effects, Bonferroni correction was utilized.

Description of Serious Adverse Event

A 59-year-old woman with treatment resistant depression had a precipitous drop in blood pressure (108/60 to 71/42 mm Hg) and heart rate (54 to 42 beats per minute) noted 5 minutes after receiving 0.3 mg/kg of DMT by intravenous over ~30 seconds (see FIG. 8). The present study responded with supportive measures. The frequency of monitoring vital signs was increased to Q1 minute. IV normal saline infusion which the subject was already receiving was increased to the maximum, and 3) her chair was reclined to a near Trendelenberg position. She denied any new symptoms/distress related to the drop in BP and heart rate. Furthermore, her oxygen saturation which was measured continuously, remained at 100%.

No other interventions were made. The drop in heart rate and blood pressure lasted approximately 5 minutes. The subject denied any symptoms throughout the experience and was verbally engageable during the event. In a detailed review after the incident, the subject revealed for the first time that she had many (>30) episodes of hypotension in the past. Most episodes were triggered by suddenly standing up. Once she recognized the pattern, she developed techniques to avoid the triggers like sitting up in bed before standing up. She also learned to kneel down when she began feeling lightheaded, until the symptoms passed. She further reported that other family members had similar episodes that were attributed to "low blood pressure."

The event was deemed serious and attributed to the effects of DMT interacting with the individual's vulnerability to autonomic instability.

One healthy subject had anticipatory anxiety and following 0.1 mg/kg DMT administration had lightheadedness, and pallor. The subject was placed in Trendelenburg position. The symptoms lasted 10 minutes.

Example 6

Referring to FIGS. 19A-19B, the present study further reports for the first-time dose-related serum DMT levels in MDD subjects who received 0.1 and 0.3 mg of IV DMT. The findings in healthy controls are mostly consistent with other studies and PK models (Callaway et al., *J Ethnopharmacol.* 1999 June; 65(3):243-56; Gallimore and Strassman, *Front. Pharmacol.,* 14 Jul. 2016). Curiously, greater variability was observed in serum concentrations of depressed individuals after receiving IV DMT. Given the increased rigor of the assay for DMT utilized in this study, it is unlikely that the variability observed in MDD subjects is spurious. It may be important to note that while DMT's acute effects had mostly resolved by +30 min time point, it is conceivable that peripheral concentration may differ from the central site of action.

Given that MDD is known to perturb numerous systems and psychopharmacological pathways, it is possible the metabolism of DMT in people with MDD may differ from healthy controls. Other causes of interindividual variability may be related to genetically driven differences in metabolism. For example, the primary enzymatic metabolizer of DMT, Monoamine Oxidase A (MAO-A) has been shown in individuals with higher neuroticism to have an aberrant haplotype with altered MAO-A functional activity (Eley et al., *Am J Med Genet B Neuropsychiatr Genet.* 2003 Jul. 1; 120B(1):90-6.). Similarly, elevated MAO-A activity was demonstrated in post-mortem investigation of the hypothalamus of those who were victims of suicide (Du et al., *Neuroreport.* 2002 Jul. 2; 13(9):1195-8). That serum DMT levels may vary will be important to account for when designing future studies with DMT in MDD.

The present study found no correlation between DMT levels and psychedelic effects measured by the ASC. However, at the 0.3 mg/kg dose, serum concentration at +30 min did positively correlate with the overall intensity of psychedelic effects. Furthermore, serum concentration at +30 min was found to correlate with thought disorder measured by the PSI.

This investigation of DMT's effects and its physiologic and psychologic correlates in MDD individuals shows that serum concentration of DMT can be useful in predicting the effects a subject may experience. Further, it presents the important consideration that studies in healthy controls in psychedelics may not be generalizable to individuals with MDD.

Enumerated Embodiments

In some aspects, the present invention is directed to the following non-limiting embodiments:

Embodiment 1: A method of treating, ameliorating, or preventing depression in a subject in need thereof, the method comprising administering parenterally to the subject an effective amount of a dimethyltryptamine (DMT) compound, wherein the DMT compound is selected from the group consisting of DMT, a DMT salt, a DMT solvate, an isotopically labelled derivative of DMT, or any mixture thereof.

Embodiment 2: The method of Embodiment 1, wherein the subject is administered the DMT compound intravenously.

Embodiment 3: The method of any one of Embodiments 1-2, wherein the amount of the DMT compound administered to the subject ranges from about 0.038 mg/kg to about 0.38 mg/kg in terms of DMT content.

Embodiment 4: The method of any one of Embodiments 1-3, wherein the subject is administered at least a first dose of an independently selected DMT compound and a second dose of an independently selected DMT compound, and wherein the dosage of the second dose in terms of DMT content is higher than the dosage of the first dose in terms of DMT content, wherein optionally the first dose and the second dose are at least 48 hours apart from each other.

Embodiment 5: The method of Embodiment 4, wherein the dosage of the first dose ranges from 0.038 mg/kg to 0.12 mg/kg in terms of DMT content, and wherein the dosage of the second dose ranges from 0.15 mg/kg to 0.38 mg/kg in terms of DMT content.

Embodiment 6: The method of any one of Embodiments 1-5, wherein the subject is not administered a monoamine oxidase inhibitor (MAOI).

Embodiment 7: The method of any one of Embodiments 1-6, wherein the DMT compound is administered as a pharmaceutical composition further comprising at least one pharmaceutically acceptable carrier.

Embodiment 8: The method of Embodiment 7, wherein the pharmaceutical composition does not comprise any other hallucinogenic or psychedelic agent besides the DMT compound.

Embodiment 9: The method of any one of Embodiments 7-8, wherein the pharmaceutical composition does not comprise any other hallucinogenic or psychedelic agent besides the DMT compound in an amount sufficient to cause a measurable antidepressive, hallucinogenic, or psychedelic effect in the subject.

Embodiment 10: The method of any one of Embodiments 7-9, wherein the pharmaceutical composition consists essentially of the DMT compound and at least one pharmaceutically acceptable carrier.

Embodiment 11: The method of any one of Embodiments 1-10, wherein the DMT compound is N,N-dimethyltryptamine hemifumarate.

Embodiment 12: The method of any one of Embodiments 1-11, wherein psychedelic effects experienced by the subject after the administration last for 60 minutes or less.

Embodiment 13: The method of any one of Embodiments 1-12, wherein the depression is a major depressive disorder (MDD).

Embodiment 14: The method of any one of Embodiments 1-13, wherein the Hamilton Rating Scale for Depression (HAMD-17) of the subject prior to the administration of the DMT or the salt, solvate, or isotopically labelled derivative thereof, or any mixture thereof, is 17 or higher.

Embodiment 15: The method of any one of Embodiments 1-14, wherein the reduction of the HAMD-17 score of the subject is 3.0 points or more the day after the administration of the DMT compound.

Embodiment 16: The method of any one of Embodiments 1-15, wherein the depression is treatment resistant or partially responsive.

Embodiment 17: The method of any one of Embodiments 1-16, wherein the subject has suffered from the depression for 10 years or more prior to the administration of the DMT compound.

Embodiment 18: The method of any one of Embodiments 1-17, wherein the subject is further administered a psychological distress medication or a hypertension medication.

Embodiment 19: The method of any one of Embodiments 1-18, wherein the subject is not provided psychotherapy at the time of the administration of the DMT compound.

Embodiment 20: The method of any one of Embodiment 1-19, wherein the peak serum level of DMT is about 300 μg/dl or less.

Embodiment 21: A kit for treating, ameliorating, or preventing depression in a subject in need thereof, the kit comprising: a dimethyltryptamine (DMT) compound selected from the group consisting of DMT, a DMT salt, a DMT solvate, an isotopically labelled derivative of DMT, or any mixture thereof, and a manual instructing that the DMT compound is to be administered parenterally to the subject in an effective amount.

Embodiment 22: The kit of Embodiment 21, wherein the manual instructs that the subject is to be administered with the DMT compound intravenously.

Embodiment 23: The kit of any one of Embodiments 21-22, wherein the manual instructs that the amount of the DMT compound to be administered to the subject ranges from about 0.038 mg/kg to about 0.38 mg/kg in terms of DMT content.

Embodiment 24: The kit of any one of Embodiments 21-23, wherein the manual instructs that the subject is to be administered with at least a first dose of an independently selected DMT compound and a second dose of an independently selected DMT compound, and wherein the dosage of the second dose in terms of DMT is higher than the dosage of the first dose in terms of DMT, wherein optionally the first dose and the second dose are at least 48 hours apart.

Embodiment 25: The kit of Embodiment 24, wherein the dosage of the first dose ranges from 0.038 mg/kg to 0.12 mg/kg in terms of DMT content, and wherein the dosage of the second dose ranges from 0.15 mg/kg to 0.38 mg/kg in terms of DMT content.

Embodiment 26: The kit of any one of Embodiments 21-25, wherein the DMT compound is not mixed with a monoamine oxidase inhibitor (MAOI).

Embodiment 27: The kit of any one of Embodiments 21-26, wherein the DMT compound is formulated as a pharmaceutical composition further comprising at least one pharmaceutically acceptable carrier.

Embodiment 28: The kit of Embodiment 27, wherein the pharmaceutical composition does not comprise any other hallucinogenic or psychedelic agent besides the DMT compound.

Embodiment 29: The kit of any one of Embodiments 27-28, wherein the pharmaceutical composition does not comprise any other hallucinogenic or psychedelic agent besides the DMT compound in an amount sufficient to cause a measurable antidepressive, hallucinogenic, or psychedelic effect in the subject.

Embodiment 30: The kit of any one of Embodiments 27-29, wherein the pharmaceutical composition consists essentially of the DMT compound and at least one pharmaceutically acceptable carrier.

Embodiment 31: The kit of any one of Embodiments 21-30, wherein the DMT compound is N,N-dimethyltryptamine hemifumarate.

Embodiment 32: The kit of any one of Embodiments 21-31, wherein, when the DMT compound is to be administered to the subject according to the instruction of the manual, psychedelic effects experienced by the subject after the administration last for 60 minutes or less.

Embodiment 33: The kit of any one of Embodiments 21-32, wherein the depression is a major depressive disorder (MDD).

Embodiment 34: The kit of any one of Embodiments 21-33, wherein the Hamilton Rating Scale for Depression (HAMD-17) of the subject prior to the administration of the DMT or the salt, solvate, or isotopically labelled derivative thereof, or any mixture thereof is 17 or higher.

Embodiment 35: The kit of any one of Embodiments 21-34, wherein, when the DMT compound is administered to the subject according to the instruction of the manual, the HAMD-17 score of the subject is reduced by 3.0 points or more the day after the administration.

Embodiment 36: The kit of any one of Embodiments 21-35, wherein the depression is treatment resistant or partially responsive.

Embodiment 37: The kit of any one of Embodiments 21-36, wherein the subject has suffered from the depression for 10 years or more.

Embodiment 38: The kit of any one of Embodiments 21-37, wherein the kit further comprises a psychological distress medication or a hypertension medication.

Embodiment 39: The kit of any one of Embodiments 21-38, wherein the manual instructs that the subject does not need to be provided psychotherapy at the time of the administration of the DMT compound.

Embodiment 40: The kit of any one of Embodiments 21-39, wherein the manual instructs that the peak serum level of DMT in the subject after the administration is about 300 μg/dl or lower.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of treating or ameliorating depression in a subject in need thereof, the method comprising:

administering parenterally to the subject an effective amount of a dimethyltryptamine (DMT) compound, wherein the DMT compound is selected from the group consisting of DMT, a DMT salt, a DMT solvate, an isotopically labelled derivative of DMT, or any mixture thereof, and wherein a dose of the DMT compound ranges from 0.038 mg/kg to 0.38 mg/kg in terms of DMT content.

2. The method of claim 1, wherein the subject is administered the DMT compound intravenously.

3. The method of claim 1, wherein the subject is administered at least a first dose of an independently selected DMT compound and a second dose of an independently selected DMT compound, and wherein the dosage of the second dose in terms of DMT content is higher than the dosage of the first dose in terms of DMT content, wherein the first dose and the second dose are at least 48 hours apart from each other.

4. The method of claim 3, wherein the dosage of the first dose ranges from 0.038 mg/kg to 0.12 mg/kg in terms of DMT content, and wherein the dosage of the second dose ranges from 0.15 mg/kg to 0.38 mg/kg in terms of DMT content.

5. The method of claim 1, wherein the subject is not administered a monoamine oxidase inhibitor (MAOI).

6. The method of claim 1, wherein the DMT compound is administered as a pharmaceutical composition further comprising at least one pharmaceutically acceptable carrier.

7. The method of claim 6, wherein the pharmaceutical composition does not comprise any other hallucinogenic or psychedelic agent besides the DMT compound.

8. The method of claim 6, wherein the pharmaceutical composition does not comprise any other hallucinogenic or psychedelic agent besides the DMT compound in an amount sufficient to cause a measurable antidepressive, hallucinogenic, or psychedelic effect in the subject.

9. The method of claim 1, wherein the pharmaceutical composition consists essentially of the DMT compound and at least one pharmaceutically acceptable carrier.

10. The method of claim 1, wherein the DMT compound (or DMT salt) is N,N-dimethyltryptamine hemifumarate.

11. The method of claim 1, wherein psychedelic effects experienced by the subject after the administration last for 60 minutes or less.

12. The method of claim 1, wherein the depression is a major depressive disorder (MDD).

13. The method of claim 1, wherein the Hamilton Rating Scale for Depression (HAMD-17) of the subject prior to the administration of the DMT or the salt, solvate, or isotopically labelled derivative thereof, or any mixture thereof, is 17 or higher.

14. The method of claim 1, wherein the reduction of the HAMD-17 score of the subject is 3.0 points or more the day after the administration of the DMT compound.

15. The method of claim 1, wherein the depression is treatment resistant or partially responsive.

16. The method of claim 1, wherein the subject has suffered from the depression for 10 years or more prior to the administration of the DMT compound.

17. The method of claim 1, wherein the subject is further administered a psychological distress medication or a hypertension medication.

18. The method of claim 1, wherein the subject is not provided psychotherapy at the time of the administration of the DMT compound.

19. The method of claim 1, wherein the peak serum level of the DMT compound in the subject after the administration is 300 g/dl or lower in terms of DMT content.

20. A kit for treating or ameliorating depression in a subject in need thereof, the kit comprising:

a dimethyltryptamine (DMT) compound selected from the group consisting of DMT, a DMT salt, a DMT solvate, an isotopically labelled derivative of DMT, or any mixture thereof; and a manual instructing that:

the DMT compound is to be administered parenterally to the subject in an effective amount, a dose of the DMT compound to be ministered ranges from 0.038 mg/kg to 0.38 mg/kg in terms of DMT content.

21. The kit of claim 20, wherein the manual instructs that the subject is to be administered with the DMT compound intravenously.

22. The kit of claim 20, wherein the manual instructs that the subject is to be administered with at least a first dose of an independently selected DMT compound and a second dose of an independently selected DMT compound, and wherein the dosage of the second dose in terms of DMT content is higher than the dosage of the first dose in terms of DMT content, wherein the first dose and the second dose are at least 48 hours apart.

23. The kit of claim 22, wherein the dosage of the first dose ranges from 0.038 mg/kg to 0.12 mg/kg, and the dosage of the second dose ranges from 0.15 mg/kg to 0.38 mg/kg in terms of DMT content.

24. The kit of claim 20, wherein the DMT compound is not mixed with a monoamine oxidase inhibitor (MAOI).

25. The kit of claim 20, wherein the DMT compound is formulated as a pharmaceutical composition further comprising at least one pharmaceutically acceptable carrier.

26. The kit of claim 25, wherein the pharmaceutical composition does not comprise any other hallucinogenic or psychedelic agent besides the DMT compound.

27. The kit of claim 25, wherein the pharmaceutical composition does not comprise any other hallucinogenic or psychedelic agent besides the DMT compound in an amount sufficient to cause a measurable antidepressive, hallucinogenic, or psychedelic effect in the subject.

28. The kit of claim 25, wherein the pharmaceutical composition consists essentially of the DMT compound and at least one pharmaceutically acceptable carrier.

29. The kit of claim 20, wherein the DMT compound is N,N-dimethyltryptamine hemifumarate.

30. The kit of claim 20, wherein, when the DMT compound is to be administered to the subject according to the instruction of the manual, psychedelic effects experienced by the subject after the administration last for 60 minutes or less.

31. The kit of claim 20, wherein the depression is a major depressive disorder (MDD).

32. The kit of claim 20, wherein the Hamilton Rating Scale for Depression (HAMD-17) of the subject prior to the administration of the DMT or the salt, solvate, or isotopically labelled derivative thereof, or any mixture thereof is 17 or higher.

33. The kit of claim 20, wherein, when the DMT compound is administered to the subject according to the instruction of the manual, the HAMD-17 score of the subject is reduced by 3.0 points or more the day after the administration.

34. The kit of claim 20, wherein the depression is treatment resistant or partially-responsive.

35. The kit of claim 20, wherein the subject has suffered from the depression for 10 years or more.

36. The kit of claim 20, wherein the kit further comprises a psychological distress medication or a hypertension medication.

37. The kit of claim 20, wherein the manual instructs that the subject does not need to be provided psychotherapy at the time of the administration of the DMT compound.

38. The kit of claim 20, wherein the manual instructs that a peak serum level of the DMT compound in the subject after the administration is 300 μg/dl or lower in terms of DMT content.

* * * * *